(12) United States Patent
Nicol et al.

(10) Patent No.: US 10,364,464 B2
(45) Date of Patent: Jul. 30, 2019

(54) COMPOSITIONS AND METHODS FOR CO-AMPLIFYING SUBSEQUENCES OF A NUCLEIC ACID FRAGMENT SEQUENCE

(75) Inventors: Robert Nicol, Cambridge, MA (US); Niall J. Lennon, Tullow (IE)

(73) Assignee: The Broad Institute, Inc., Cambridge, MA (US)

(*) Notice: Subject to any disclaimer, the term of this patent is extended or adjusted under 35 U.S.C. 154(b) by 202 days.

(21) Appl. No.: 14/237,603

(22) PCT Filed: Aug. 8, 2012

(86) PCT No.: PCT/US2012/049981
§ 371 (c)(1),
(2), (4) Date: May 5, 2014

(87) PCT Pub. No.: WO2013/022961
PCT Pub. Date: Feb. 14, 2013

(65) Prior Publication Data
US 2014/0243242 A1    Aug. 28, 2014

Related U.S. Application Data

(60) Provisional application No. 61/521,170, filed on Aug. 8, 2011.

(51) Int. Cl.
*C12Q 1/68*    (2018.01)
*C12Q 1/6874*    (2018.01)
(Continued)

(52) U.S. Cl.
CPC ....... *C12Q 1/6874* (2013.01); *C12N 15/1065* (2013.01); *C12Q 1/6869* (2013.01)

(58) Field of Classification Search
USPC ................................. 435/6.12, 91.2
See application file for complete search history.

(56) References Cited

U.S. PATENT DOCUMENTS 5,639,603 A    6/1997   Dower et al.
5,683,869 A    11/1997  Ramsay Shaw et al.
(Continued)

FOREIGN PATENT DOCUMENTS

JP    2008-545448 A    12/2008
WO   WO 02061143 A2 *   8/2002   ........... C12Q 1/6809
(Continued)

OTHER PUBLICATIONS

"Random Primers" [online] Aug. 28, 2005 [retrieved on Apr. 28, 2013] retrieved from http://web.archive.org/web/20050828014046/http://www.genelink.com/geneprodsite/category.asp?c=81.*
(Continued)

*Primary Examiner* — Samuel C Woolwine
(74) *Attorney, Agent, or Firm* — Wolf, Greenfield & Sacks, P.C.

(57) ABSTRACT

The present invention is related to genomic nucleotide sequencing. In particular, the invention describes a single reaction method to co-amplify multiple subsequences of a nucleic acid fragment sequence (i.e., for example, at least two read pairs from a single library insert sequence). Nucleic acid fragment sequences may include, but are not limited to, localizing library insert sequences and/or unique read pair sequences in specific orientations on a single emulsion polymerase chain reaction bead. Methods may include, but are not limited to, annealing, melting, digesting, and/or reannealing high throughput sequencing primers to high throughput sequencing primer binding sites. The compositions and methods disclosed herein contemplate sequencing complex genomes, amplified genomic regions, as well as detecting chromosomal structural rearrangements that are compatible with massively parallel high throughput sequencing platforms as well as ion semiconductor matching sequencing platforms (i.e., for example, Ion Torrent platforms).

17 Claims, 11 Drawing Sheets

Specification includes a Sequence Listing.

(51) Int. Cl.
C12Q 1/6869 (2018.01)
C12N 15/10 (2006.01)

(56) References Cited

U.S. PATENT DOCUMENTS

| | | | |
|---|---|---|---|
| 5,859,231 | A | 1/1999 | Shaw et al. |
| 5,874,259 | A | 2/1999 | Szybalski |
| 6,165,778 | A | 12/2000 | Kedar |
| 6,376,178 | B1 | 4/2002 | Shaw et al. |
| 6,436,635 | B1 | 8/2002 | Fu et al. |
| 6,709,861 | B2 | 3/2004 | Mead et al. |
| 6,991,903 | B2 | 1/2006 | Fu et al. |
| 7,211,414 | B2 | 5/2007 | Hardin et al. |
| 7,303,885 | B1 | 12/2007 | Brunner et al. |
| 7,627,437 | B2 | 12/2009 | Forney et al. |
| 7,833,769 | B2 | 11/2010 | Anton et al. |
| 7,964,349 | B2 | 6/2011 | Bell et al. |
| 9,738,930 | B2 | 8/2017 | Nicol et al. |
| 2007/0054311 | A1 | 3/2007 | Kamberov et al. |
| 2007/0269870 | A1 | 11/2007 | Church et al. |
| 2009/0093378 | A1* | 4/2009 | Bignell .............. C12N 15/1093 506/23 |
| 2009/0202984 | A1 | 8/2009 | Cantor |
| 2010/0016170 | A1 | 1/2010 | Farnet et al. |
| 2010/0055702 | A1 | 3/2010 | Battle et al. |
| 2010/0222238 | A1 | 9/2010 | Smith et al. |
| 2010/0240101 | A1 | 9/2010 | Lieberman et al. |
| 2010/0273219 | A1 | 10/2010 | May et al. |
| 2010/0273662 | A1 | 10/2010 | Gormley et al. |
| 2014/0031241 | A1 | 1/2014 | Nicol et al. |
| 2014/0228223 | A1 | 8/2014 | Gnirke et al. |

FOREIGN PATENT DOCUMENTS

WO WO 2006/084132 A2 8/2006
WO WO 2008069906 A2 * 6/2008 ........... C12Q 1/6809

OTHER PUBLICATIONS

International Search Report and Written Opinion dated Nov. 2, 2012 for Application No. PCT/US2012/49981.
International Preliminary Report on Patentability dated Feb. 20, 2014 for Application No. PCT/US2012/49981.
Adams et al., The genome sequence of Drosophila melanogaster. Science. Mar. 24, 2000;287(5461):2185-95.
Anderson, Shotgun DNA sequencing using cloned DNase I-generated fragments. Nucleic Acids Res. Jul. 10, 1981;9(13):3015-27.
Ansorge et al., Next-generation DNA sequencing techniques. N Biotechnol. Apr. 2009;25(4):195-203. doi: 10.1016/j.nbt.2008.12.009. Epub Feb. 3, 2009. Review.
Bentley et al., Accurate whole human genome sequencing using reversible terminator chemistry. Nature. Nov. 6, 2008;456(7218):53-9. doi: 10.1038/nature07517.
Braslavsky et al., Sequence information can be obtained from single DNA molecules. Proc Natl Acad Sci U S A. Apr. 1, 2003;100(7):3960-4. Epub Mar. 21, 2003.
Campbell et al., Identification of somatically acquired rearrangements in cancer using genome-wide massively parallel paired-end sequencing. Nat Genet. Jun. 2008;40(6):722-9. doi: 10.1038/ng.128.
Church et al., Genomes for all. Sci Am. Jan. 2006;294(1):46-54.
Cloonan et al., Stem cell transcriptome profiling via massive-scale mRNA sequencing. Nat Methods. Jul. 2008;5(7):613-9. doi: 10.1038/nmeth.1223.
Dressman et al., Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Edwards et al., Automated DNA sequencing of the human HPRT locus. Genomics. Apr. 1990;6(4):593-608.
Edwards et al., Closure strategies for random DNA sequencing. Methods: A Companion to Methods in Enzymology. 1991;3:41-7.
Eid et al., Real-time DNA sequencing from single polymerase molecules. Science. Jan. 2, 2009;323(5910):133-8. doi: 10.1126/science.1162986.
Fleischmann et al., Whole-genome random sequencing and assembly of Haemophilus influenzae Rd. Science. Jul. 28, 1995;269(5223):496-512.
Fullwood et al., Next-generation DNA sequencing of paired-end tags (PET) for transcriptome and genome analyses. Genome Res. Apr. 2009;19(4):521-32. doi: 10.1101/gr.074906.107. Review.
Gibbs et al., Evolutionary and biomedical insights from the rhesus macaque genome. Science. Apr. 13, 2007;316(5822):222-34.
Harris et al., Single-molecule DNA sequencing of a viral genome. Science. Apr. 4, 2008;320(5872):106-9. doi: 10.1126/science.1150427.
Ju et al., Four-color DNA sequencing by synthesis using cleavable fluorescent nucleotide reversible terminators. Proc Natl Acad Sci U S A. Dec. 26, 2006;103(52):19635-40. Epub Dec. 14, 2006.
Korbel et al., Paired-end mapping reveals extensive structural variation in the human genome. Science. Oct. 19, 2007;318(5849):420-6. Epub Sep. 27, 2007.
Lundquist et al., Parallel confocal detection of single molecules in real time. Opt Lett. May 1, 2008;33(9):1026-8.
Mardis et al., Next-generation DNA sequencing methods. Annu Rev Genomics Hum Genet. 2008;9:387-402. doi: 10.1146/annurev.genom.9.081307.164359. Review.
Margulies et al., Genome sequencing in microfabricated high-density picolitre reactors. Nature. Sep. 15, 2005;437(7057):376-80. Epub Jul. 31, 2005. Erratum in: Nature. May 4, 2006;441(7089):120.
Metzker, Sequencing technologies—the next generation. Nat Rev Genet. Jan. 2010;11(1):31-46. doi: 10.1038/nrg2626. Epub Dec. 8, 2009. Review.
Olsvik et al., Use of automated sequencing of polymerase chain reaction-generated amplicons to identify three types of cholera toxin subunit B in Vibrio cholerae O1 strains. J Clin Microbiol. Jan. 1993;31(1):22-5.
Pemov et al., DNA analysis with multiplex microarray-enhanced PCR. Nucleic Acids Res. Jan. 20, 2005;33(2):e11.
Porreca et al., Polony DNA sequencing. Curr Protoc Mol Biol. Nov. 2006;Chapter 7:Unit 7.8. doi: 10.1002/0471142727.mb0708s76. Review.
Roach et al., Pairwise end sequencing: a unified approach to genomic mapping and sequencing. Genomics. Mar. 20, 1995;26(2):345-53.
Ronaghi et al., Real-time DNA sequencing using detection of pyrophosphate release. Anal Biochem. Nov. 1, 1996;242(1):84-9.
Rothberg et al., An integrated semiconductor device enabling non-optical genome sequencing. Nature. Jul. 20, 2011;475(7356):348-52. Supplementary Information, 25 pages. doi: 10.1038/nature10242.
Shendure et al., Accurate multiplex polony sequencing of an evolved bacterial genome. Science. Sep. 9, 2005;309(5741):1728-32.
Shendure et al., Next-generation DNA sequencing. Nat Biotechnol. Oct. 2008;26(10):1135-45. doi: 10.1038/nbt1486.
Tawfik et al., Man-made cell-like compartments for molecular evolution. Nat Biotechnol. Jul. 1998;16(7):652-6.
Valouev et al., A high-resolution, nucleosome position map of C. elegans reveals a lack of universal sequence-dictated positioning. Genome Res. Jul. 2008;18(7):1051-63. doi: 10.1101/gr.076463.108.
Wheeler et al., The complete genome of an individual by massively parallel DNA sequencing. Nature. Apr. 17, 2008;452(7189):872-6. doi: 10.1038/nature06884.
Xu et al., Dual primer emulsion PCR for next-generation DNA sequencing. Biotechniques. May 2010;48(5):409-12. doi: 10.2144/000113423.
[No Author Listed], Applied Biosystems SOLiDTM 4 System Library Preparation Guide, Chapter 3: Mate-Paired Library Preparation (Apr. 2010). 86 pages.
[No Author Listed], Applied Biosystems SOLiD™ 4 System. Library Preparation Guide. Applied Biosystems. Apr. 2010 259 pages.

(56) References Cited

OTHER PUBLICATIONS

[No Author Listed], International Human Genome Sequencing Consortium. Finishing the euchromatic sequence of the human genome. Nature. Oct. 21, 2004;431(7011):931-45.

Bates et al., Double cos site vectors: simplified cosmid cloning. Gene. Dec. 1983;26(2-3):137-46. PubMed PMID: 6323255.

Brenner et al., Gene expression analysis by massively parallel signature sequencing (MPSS) on microbead arrays. Nat Biotechnol. Jun. 2000;18(6):630-4. Erratum in: Nat Biotechnol Oct. 2000;18(10):1021.

Butler et al., ALLPATHS: de novo assembly of whole-genome shotgun microreads. Genome Res. May 2008;18(5):810-20. doi: 10.1101/gr.7337908. Epub Mar. 13, 2008.

Collins et al., (1987) Construction of a general human chromosome jumping library, with application to cystic fibrosis. Science 235(4792):1046-1049.

Collins et al., Directional cloning of DNA fragments at a large distance from an initial probe: a circularization method. Proc Natl Acad Sci U S A. Nov. 1984;81(21):6812-6.

David et al., An improved copy control fosmid vector maximizes end-sequencing results. Epicentre Forum, 2006;13(1):17.

Evans et al., High efficiency vectors for cosmid microcloning and genomic analysis. Gene. Jun. 30, 1989;79(1):9-20.

Fedurco et al., BTA, a novel reagent for DNA attachment on glass and efficient generation of solid-phase amplified DNA colonies. Nucleic Acids Res. Feb. 9, 2006;34(3):e22.

Gnerre et al., High-quality draft assemblies of mammalian genomes from massively parallel sequence data. Proc Natl Acad Sci U S A. Jan. 25, 2011;108(4):1513-8. doi:10.1073/pnas.1017351108. Epub Dec. 27, 2010.

Godiska et al., Linear plasmid vector for cloning of repetitive or unstable sequences in *Escherichia coli*. Nucleic Acids Res. Apr. 2010;38(6):e88. doi: 10.1093/nar/gkp1181. Epub Dec. 29, 2009.

Hall., Advanced sequencing technologies and their wider impact in microbiology. J Exp Biol. May 2007;210(Pt 9):1518-25.

Kim et al., Stable propagation of cosmid sized human DNA inserts in an F factor based vector. Nucleic Acids Res. Mar. 11, 1992;20(5):1083-5.

Levy et al. The diploid genome sequence of an individual human. PLoS Biol. Sep. 4, 2007;5(10):e254. pp. 2113-2144.

Li et al., De novo assembly of human genomes with massively parallel short read sequencing. Genome Res. Feb. 2010;20(2):265-72. doi:10.1101/gr.097261.109. Epub Dec. 17, 2009.

Li et al., The sequence and de novo assembly of the giant panda genome. Nature. Jan. 21, 2010;463(7279):311-7. doi:10.1038/nature08696. Epub Dec. 13, 2009.

Lindblad-Toh et al., Genome sequence, comparative analysis and haplotype structure of the domestic dog. Nature. Dec. 8, 2005;438(7069):803-19.

Lozzio et al., Human chronic myelogenous leukemia cell-line with positive Philadelphia chromosome. Blood. Mar. 1975,45(3):321-34.

MacCallum et al., ALLPATHS 2: small genomes assembled accurately and with high continuity from short paired reads. Genome Biol. 2009;10(10):R103. doi: 10.1186/gb-2009-10-10-r103. Epub Oct. 1, 2009.

McKernan et al. (2009) Sequence and structural variation in a human genome uncovered by short-read, massively parallel ligation sequencing using two-base encoding, Genome Res. Sep. 2009;19(9):1527-41. doi: 10.1101/gr.091868.109. Epub Jun. 22, 2009.

Mikkelsen et al., Genome of the marsupial Monodelphis domestica reveals innovation in non-coding sequences. Nature. May 10, 2007;447(7141):167-77.

Nowrousian et al., De novo assembly of a 40 Mb eukaryotic genome from short sequence reads: Sordaria macrospora, a model organism for fungal morphogenesis. PLoS Genet. Apr. 8, 2010;6(4):e1000891. doi:10.1371/journal.pgen.1000891.

Ochman et al., Genetic applications of an inverse polymerase chain reaction. Genetics Nov. 1988;120(3):621-3.

Poustka et al., (1987) Construction and use of human chromosome jumping libraries from NotI-digested DNA. Nature. Jan. 22-28, 1987;325(6102):353-5.

Ronaghi et al., Analyses of secondary structures in DNA by pyrosequencing. Anal Biochem. Feb. 1, 1999;267(1):65-71.

Schuster et al., Complete Khoisan and Bantu genomes from southern Africa. Nature. Feb. 18, 2010;463(7283):943-7. doi:10.1038/nature08795.

Waterston et al., Initial sequencing and comparative analysis of the mouse genome. Nature. Dec. 5, 2002;420(6915):520-62.

Williams et al., Paired-end sequencing of Fosmid libraries by Illumina. Genome Res. Nov. 2012;22(11):2241-9. doi:10.1101/gr.138925.112. Epub Jul. 16, 2012. Supplemental Material Included. 10 Pages.

Xu et al., Dual primer emulsion PCR for next-generation DNA sequencing. Biotechniques. May 2010;48(5):409-12. Supplementary Material: Biotechniques. May 2010;48(5): 351-3.

Zerbino et al., Velvet: algorithms for de novo short read assembly using de Bruijn graphs. Genome Res. May 2008;18(5):821-9. doi: 10.1101/gr.074492.107. Epub Mar. 18, 2008.

Zhang et al., A novel degradation pathway of chloroaniline in *Diaphorobacter* sp. PCA039 entails initial hydroxylation. World J Microbiol Biotechnol. Apr. 2010;26(4):665-73.

\* cited by examiner

SEQUENCE LISTING

```
<160> NUMBER OF SEQ ID NOS: 16

<210> SEQ ID NO 1
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(6)
<223> OTHER INFORMATION: n is a, c, g, or t

<400> SEQUENCE: 1 nnnnnn                                                                     6

<210> SEQ ID NO 2
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(7)
<223> OTHER INFORMATION: n is a, c, g, or t

<400> SEQUENCE: 2 nnnnnnn                                                                    7

<210> SEQ ID NO 3
<211> LENGTH: 8
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(8)
<223> OTHER INFORMATION: n is a, c, g, or t

<400> SEQUENCE: 3 nnnnnnnn                                                                      8

<210> SEQ ID NO 4
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: n is a, c, g, or t

<400> SEQUENCE: 4 nnnnnnnnn                                                                     9

<210> SEQ ID NO 5
<211> LENGTH: 6
<212> TYPE: DNA
<213> ORGANISM: Artificial Sequence
<220> FEATURE:
<223> OTHER INFORMATION: Synthetic

<400> SEQUENCE: 5 agtcct                                                                        6

<210> SEQ ID NO 6
<211> LENGTH: 7
<212> TYPE: DNA
<213> ORGANISM: Artificial Sequence
<220> FEATURE:
<223> OTHER INFORMATION: Synthetic

<400> SEQUENCE: 6 tcctgag                                                                       7

<210> SEQ ID NO 7
<211> LENGTH: 8
<212> TYPE: DNA
<213> ORGANISM: Artificial Sequence
<220> FEATURE:
<223> OTHER INFORMATION: Synthetic

<400> SEQUENCE: 7 tgatccat                                                                      8

<210> SEQ ID NO 8
<211> LENGTH: 9
<212> TYPE: DNA
<213> ORGANISM: Artificial Sequence
<220> FEATURE:
<223> OTHER INFORMATION: Synthetic

<400> SEQUENCE: 8 cgtacgtct                                                                     9

<210> SEQ ID NO 9
<211> LENGTH: 8
<212> TYPE: DNA
<213> ORGANISM: Artificial Sequence
```

```
<220> FEATURE:
<223> OTHER INFORMATION: Synthetic

<400> SEQUENCE: 9 ttgagcct                                                                    8

<210> SEQ ID NO 10
<211> LENGTH: 8
<212> TYPE: DNA
<213> ORGANISM: Artificial Sequence
<220> FEATURE:
<223> OTHER INFORMATION: Synthetic

<400> SEQUENCE: 10 agttgctt                                                                    8

<210> SEQ ID NO 11
<211> LENGTH: 8
<212> TYPE: DNA
<213> ORGANISM: Artificial Sequence
<220> FEATURE:
<223> OTHER INFORMATION: Synthetic

<400> SEQUENCE: 11 ccagttag                                                                    8

<210> SEQ ID NO 12
<211> LENGTH: 8
<212> TYPE: DNA
<213> ORGANISM: Artificial Sequence
<220> FEATURE:
<223> OTHER INFORMATION: Synthetic

<400> SEQUENCE: 12 accaactg                                                                    8

<210> SEQ ID NO 13
<211> LENGTH: 8
<212> TYPE: DNA
<213> ORGANISM: Artificial Sequence
<220> FEATURE:
<223> OTHER INFORMATION: Synthetic

<400> SEQUENCE: 13 gtataaca                                                                    8

<210> SEQ ID NO 14
<211> LENGTH: 8
<212> TYPE: DNA
<213> ORGANISM: Artificial Sequence
<220> FEATURE:
<223> OTHER INFORMATION: Synthetic

<400> SEQUENCE: 14 caggagcc                                                                    8

<210> SEQ ID NO 15
<211> LENGTH: 6
<212> TYPE: DNA
<213> ORGANISM: Artificial Sequence
<220> FEATURE:
<223> OTHER INFORMATION: Synthetic

<400> SEQUENCE: 15 tgatcc                                                                      6
```

```
<210> SEQ ID NO 16
<211> LENGTH: 25
<212> TYPE: DNA
<213> ORGANISM: Artificial Sequence
<220> FEATURE:
<223> OTHER INFORMATION: Synthetic

<400> SEQUENCE: 16
atgcttcggc aagactcaaa aaata                                       25
```

COMPOSITIONS AND METHODS FOR CO-AMPLIFYING SUBSEQUENCES OF A NUCLEIC ACID FRAGMENT SEQUENCE

RELATED APPLICATIONS

This application is a national stage filing under 35 U.S.C. § 371 of International Application No. PCT/US2012/049981 filed Aug. 8, 2012, which was published under PCT Article 21(2) in English, and which claims the benefit of U.S. Provisional Application Ser. No. 61/521,170, filed on Aug. 8, 2011, both entitled "COMPOSITIONS AND METHODS FOR CO-AMPLIFYING SUBSEQUENCES OF A NUCLEIC ACID FRAGMENT SEQUENCE", the entire contents of each of which are incorporated by reference herein.

GOVERNMENT SUPPORT

This invention was made with government support under Grant No. HG003067 awarded by the National Institutes of Health. The government has certain rights in the invention.

FIELD OF THE INVENTION

The present invention is related to genomic nucleotide sequencing. In particular, the invention describes a single reaction method to co-amplify multiple subsequences of a nucleic acid fragment sequence (i.e., for example, at least two read pairs from a single library insert sequence). Nucleic acid fragment sequences may include, but are not limited to, localizing library insert sequences and/or unique read pair sequences in specific orientations on a single emulsion polymerase chain reaction bead. Methods may include, but are not limited to, annealing, melting, digesting, and/or reannealing high throughput sequencing primers to high throughput sequencing primer binding sites. The compositions and methods disclosed herein contemplate sequencing complex genomes, amplified genomic regions, as well as detecting chromosomal structural rearrangements that are compatible with massively parallel high throughput sequencing platforms as well as ion semiconductor matching sequencing platforms (i.e., for example, Ion Torrent platforms).

BACKGROUND

Recent advances in sequencing technology have rapidly driven down the cost of DNA sequence data and yield an unrivalled resource of genetic information. Individual genomes can be characterized, while genetic variation may be studied in populations and disease. Until recently, the scope of sequencing projects was limited by the cost and throughput of Sanger sequencing. The raw data for the three billion base (3 gigabase (Gb)) human genome sequence was generated over several years for ~$300 million using several hundred capillary sequencers. International Human Genome Sequencing Consortium, "Finishing the euchromatic sequence of the human genome" *Nature* 431:931-945 (2004). More recently, an individual human genome sequence has been determined for ~$10 million by capillary sequencing. Levy et al., "The diploid genome sequence of an individual human" *PLoS Biol.* 5:e254 (2007). Several new approaches at varying stages of development aim to increase sequencing throughput and reduce cost. Margulies et al., "Genome sequencing in microfabricated high-density picoliter reactors" *Nature* 437:376-380 (2005); Shendure et al., "Accurate multiplex polony sequencing of an evolved bacterial genome" *Science* 309:1728-1732 (2005); Harris et al., "Single-molecule DNA sequencing of a viral genome" *Science* 320:106-109 (2008); and Lundquist et al., "Parallel confocal detection of single molecules in real time" *Opt. Lett.* 33:1026-1028 (2008). These techniques increase parallelization markedly by imaging many DNA molecules simultaneously. One instrument run produces typically thousands or millions of sequences that are shorter than capillary reads. Another human genome sequence was recently determined using one of these approaches. Wheeler et al., "The complete genome of an individual by massively parallel DNA sequencing" *Nature* 452:872-876 (2008). Moreover, an international consortium is currently in the process of determining the genome sequence of at least a thousand different human individuals (1000 genomes.org/page.php?page=home). These human genome sequences are typically based on the pre-existing human reference sequence and are not assembled de novo (i.e., without prior knowledge of the reference sequence)

However, further improvements are necessary to improve the efficiency of these massively parallel sequencing systems to enable routine sequencing and assembly of complex genomes de novo (i.e., without a pre-existing reference sequence). Essentially all methods for assembling genomes de novo require pairs of sequencing reads that have an a priori defined orientation and spacing in the underlying genome. Short-distance read pairs (i.e., for example 25-500 bps) are usually employed, even to provide information regarding long-range contiguity of genome assemblies. Using such short-distance read pairs, genome assemblies remain highly fragmented. Approaches that improve amplification yield and sequencing efficiency of massively-parallel sequencers using short-distance read pairs would greatly improve the quality of genome assemblies.

The ability to produce sequence reads from distal ends of a single DNA fragment (paired-end sequencing) is extremely useful for many down stream analyses. Currently there are no sequencing by polymerase synthesis commercially available methods for effective paired-end sequencing from beads on any of the established bead-based sequencing technologies (AB Solid, Roche/454, and Ion Torrent).

SUMMARY OF THE INVENTION

The present invention is related to genomic nucleotide sequencing. In particular, the invention describes a single reaction method to co-amplify multiple subsequences of a nucleic acid fragment sequence (i.e., for example, at least two read pairs from a single library insert sequence). Nucleic acid fragment sequences may include, but are not limited to, localizing library insert sequences and/or unique read pair sequences in specific orientations on a single emulsion polymerase chain reaction bead. Methods may include, but are not limited to, annealing, melting, digesting, and/or reannealing high throughput sequencing primers to high throughput sequencing primer binding sites. The compositions and methods disclosed herein contemplate sequencing complex genomes, amplified genomic regions, as well as detecting chromosomal structural rearrangements that are compatible with massively parallel high throughput sequencing platforms as well as ion semiconductor matching sequencing platforms (i.e., for example, Ion Torrent platforms).

In one embodiment, the present invention contemplates a method, comprising: a) providing; i) a solid substrate that can be attached to at least one labeled nucleic acid sequence;

ii) a plurality of nucleic acid sequences each further comprising at least one primer sequence, wherein said plurality of nucleic acid sequences comprise labeled nucleic acid sequences each further comprising an attachment feature; and ii) a plurality of nucleic acid fragments, wherein said plurality of nucleic acid fragments comprise a plurality of subsequences; b) annealing said plurality of nucleic acid fragments to said at least one primer sequence of said at least one nucleic acid sequences under conditions that generate a plurality of amplified nucleic acid fragments, wherein said amplified nucleic acid fragments are labeled fragments which comprise labeled nucleic acid sequences; and c) combining said labeled nucleic acid sequences with the solid substrate under conditions that attach. In one embodiment, the label of the labeled nucleic acid sequence comprises a label selected from the group consisting of biotin, universal primers, and nucleic acid barcodes. In one embodiment, the plurality of nucleic acid sequences comprises a mixture of labeled and non-labeled nucleic acid sequences. In one embodiment, the ratio of the mixture of labeled and non-labeled nucleic acid sequences is between 30:70 and 70:30. In one embodiment, the labeled nucleic acid sequence is attached to the solid substrate by complementary hybridization, ligation or chemical bond. In one embodiment, the labeled nucleic acid sequence is attached to the solid substrate with a linker. In one embodiment, the linker comprises a streptavidin molecules, a nucleic acid sequence, a thioester linker sequence or a ribonucleic acid linker sequence. In one embodiment, the solid substrate is selected from the group consisting of a bead and a microwell or a surface. In one embodiment, the solid substrate is combined with the labeled fragments before amplification. In one embodiment, the primer sequence comprises at least one random primer sequence selected from the group consisting of hexamer, heptamer, octomer and nonomer. In one embodiment, the plurality of nucleic acid fragments are derived from a biological sample selected from the group consisting of a single genome, a single nucleic acid library, and a single nucleic acid library insert sequence. In one embodiment, each of said plurality of nucleic acid fragments is circularized. In one embodiment, the plurality of nucleic acid fragments is ligated to at least one barcode. In one embodiment, the barcoded nucleic acid fragment is amplified. In one embodiment, the plurality of subsequences comprise a first subsequence having a first read pair sequence. In one embodiment, the plurality of subsequences comprise a second subsequence having a second read pair sequence. In one embodiment, the first read pair sequence comprises a first high throughput sequencing primer binding site. In one embodiment, the second read pair sequence comprises a second high throughput sequencing primer binding site. In one embodiment, the method further provides at least one primer selected from the group consisting of a first high throughput sequencing primer and a second high throughput sequencing primer. In one embodiment, the method further comprises the step of annealing said first high throughput sequencing primer binding site to said first high throughput sequencing primer, under conditions such that said first read sequence is amplified. In one embodiment, the method further comprises the step of annealing said second high throughput sequencing primer binding site to said second high throughput sequencing primer, under conditions such that said second read sequence is amplified. In one embodiment, the first and second high throughput sequencing primers are selected from the group consisting of 454 sequencing primers, Illumina sequencing primers, SOLiD sequencing primers, and ion semiconduction sequencing primers.

In one embodiment, the present invention contemplates a method, comprising: a) providing; i) a solid substrate coated with a plurality of linkers, wherein each of said plurality of said linkers comprise at least one random primer sequence; and, ii) a plurality of circularized nucleic acid fragments, wherein said plurality of circularized nucleic acid fragments comprise a plurality of subsequences; and b) annealing said plurality of circularized nucleic acid fragments to said at least one random primer sequence under conditions that generate a plurality of amplified nucleic acid fragments. In one embodiment the random primer sequence comprises a biotin molecule. In one embodiment, the linker comprises a streptavidin molecule. In one embodiment, the solid substrate is selected from the group consisting of a bead and a microwell. In one embodiment, the plurality of circularized nucleic acid fragments are derived from a biological sample selected from the group consisting of a single genome, a single nucleic acid library, and a single nucleic acid library insert sequence. In one embodiment, each of said plurality of amplified nucleic acid fragments is attached to said solid substrate. In one embodiment, the linker is selected from the group consisting of a nucleic acid sequence, a thioester linker sequence and a ribonucleic acid linker sequence. In one embodiment, the plurality of subsequences comprise a first subsequence having a first read pair sequence. In one embodiment, the plurality of subsequences comprise a second subsequence having a second read pair sequence. In one embodiment, the first read pair sequence comprises a first high throughput sequencing primer binding site. In one embodiment, the second read pair sequence comprises a second high throughput sequencing primer binding site. In one embodiment, the method further provides at least one primer selected from the group consisting of a first high throughput sequencing primer and a second high throughput sequencing primer. In one embodiment, the method further comprises the step of annealing said first high throughput sequencing primer binding site to said first high throughput sequencing primer, under conditions such that said first read sequence is amplified. In one embodiment, the method further comprises the step of annealing said second high throughput sequencing primer binding site to said second high throughput sequencing primer, under conditions such that said second read sequence is amplified. In one embodiment, the first and second high throughput sequencing primers are selected from the group consisting of 454 sequencing primers, Illumina sequencing primers, SOLiD sequencing primers, and ion semiconduction sequencing primers.

In one embodiment, the present invention contemplates a kit comprising: a) a first container comprising a solid substrate capable of attaching at least one nucleic acid fragment sequence by a linker, wherein said nucleic acid fragment sequence comprises a plurality of subsequences; b) a second container comprising a first high throughput sequencing primer capable of amplifying a first subsequence of said plurality of subsequences; c) a third container comprising a second high throughput sequencing primer capable of amplifying a second subsequence of said plurality of subsequences; d) a fourth container comprising at least one linker; and e) instructions for co-amplifying said first and second subsequences with said first and second high throughput sequencing primers in a single reaction mixture. In one embodiment, the solid substrate is selected from the group consisting of a bead and a microwell. In one embodiment, the linker comprises a random primer sequence. In one embodiment, the random primer sequence comprises a biotin molecule. In one embodiment, the at least one linker is selected from the group consisting of a streptavidin molecule, a thioester sequence and a ribonucleic acid sequence. In one embodiment, the plurality of subsequences comprise a nucleic acid sequence selected from the group consisting of a first read pair sequence and a second read pair sequence. In one embodiment, the instructions further provide ligating said first read pair sequence to said first high throughput sequencing primer and said second read pair sequence to said second high throughput sequencing primer. In one embodiment, the instructions further provide amplifying said first read pair sequence with said first high throughput sequencing primer and said second read pair sequence with said second high throughput sequencing primer. In one embodiment, the kit further provides a fifth container comprising enzymes and reagents capable of performing a polymerase chain reaction. In one embodiment, the first and second high throughput sequencing primers are selected from the group consisting of 454 sequencing primers, Illumina sequencing primers, SOLiD sequencing primers, and ion semiconduction sequencing primers. In one embodiment, the linker sequence is selected from the grouped consisting of a nucleic acid sequence, a thioester sequence and a ribonucleic acid sequence.

In one embodiment, the present invention contemplates a method, comprising: a) providing: i) a solid substrate attached to at least one nucleic acid fragment sequence by a linker sequence, wherein the nucleic acid fragment sequence comprises a plurality of subsequences; ii) a first primer capable of amplifying a first subsequence of the plurality of subsequences; and iii) a second primer capable of amplifying a second subsequence of the plurality of subsequences; and b) co-amplifying said first and second subsequences with said first and second primers. In one embodiment, each of the at least one nucleic acid fragment sequences is derived from a single genome. In one embodiment, each of the at least one nucleic acid fragment sequences is derived from a single library. In one embodiment, each of the at least one nucleic acid fragment sequences is derived from a library nucleic acid insert sequence. In one embodiment, the solid substrate comprises a bead. In one embodiment, the bead is an emulsion polymerase chain reaction bead. In one embodiment, the solid substrate comprises a microwell. In one embodiment, the multiple subsequences are attached to said solid substrate as separate sequences. In one embodiment, the multiple subsequences are attached to said solid substrates as a single sequence. In one embodiment, the multiple subsequences comprise a first read pair sequence and a second read pair sequence. In one embodiment, the first read pair sequence is ligated to a first high throughput sequencing primer binding site. In one embodiment, the second read pair sequence is ligated to a second high throughput sequencing primer binding site. In one embodiment, the first primer comprises a first high throughput sequencing primer capable of annealing to the first high throughput sequencing primer binding site to generate an amplified first read sequence (Read 1). In one embodiment, the method further comprises the step of melting the first high throughput sequencing primer from the amplified first read sequence. In one embodiment, the method further comprises the step of enzymatically digesting the first high throughput sequencing primer from the amplified first read sequence. In one embodiment, the second primer comprises a second high throughput sequencing primer capable of annealing to the second high throughput sequencing primer binding site to generate an amplified second read sequence (Read 2). In one embodiment, the method further comprises the step of melting the second high throughput sequencing primer from the amplified second read sequence. In one embodiment, the method further comprises the step of enzymatically digesting the second high throughput sequencing primer from the second amplified read sequence. In one embodiment, the digesting comprises an exonuclease enzyme (e.g., exonuclease III). In one embodiment, the digesting comprises a ribonuclease enzyme. In one embodiment, the first and second high throughput sequencing primers are 454 sequencing primers. In one embodiment, the first and second high throughput sequencing primers are Illumina sequencing primers. In one embodiment, the first and second high throughput sequencing primers are SOLiD sequencing primers. In one embodiment, the first and second high throughput sequencing primers are ion semiconductor sequencing primers. In one embodiment, the co-amplification is performed in a single reaction mixture.

In one embodiment, the present invention contemplates a composition comprising a bead coated with at least one linker nucleic acid sequence ligated to at least one nucleic acid fragment sequence. In one embodiment, each of the at least one nucleic acid fragment sequences is derived from a single genome. In one embodiment, each of the at least one nucleic acid fragment sequences is derived from a single library. In one embodiment, each of the at least one nucleic acid fragment sequences is derived from a library insert sequence. In one embodiment, a first nucleic acid fragment sequence of the at least one nucleic acid fragment sequences comprises a first subsequence. In one embodiment, a second nucleic acid fragment sequence of the at least one nucleic acid fragment sequences comprises a second subsequence. In one embodiment, the first subsequence is ligated to a first high throughput sequencing primer binding site. In one embodiment, the second subsequence is ligated to a second high throughput sequencing primer binding site. In one embodiment, the first subsequence comprises a first read pair sequence. In one embodiment, the second subsequence comprises a second read pair sequence. In one embodiment, the composition further comprises at least one high throughput sequencing primer. In one embodiment, the composition further comprises at least one amplified read sequence. In one embodiment, the at least one high throughput sequencing primer is a 454 sequencing primer. In one embodiment, the at least one high throughput sequencing primer is an Illumina sequencing primer. In one embodiment, the at least one high throughput sequencing primer is a SOLiD sequencing primer. In one embodiment, the at least one high throughput sequencing primer is an ion semiconductor sequencing primer.

In one embodiment, the present invention contemplates a method comprising: a) providing; i) a composition comprising a bead coated with at least one linker nucleic acid sequence ligated to at least one nucleic acid fragment sequence; ii) a first high throughput sequencing primer binding site sequence ligated to a first nucleic acid sequence of the at least one nucleic acid sequence; iii) a second high throughput sequencing primer binding site sequence ligated to a second nucleic acid sequence of the at least one nucleic acid sequence; iv) a first high throughput sequencing primer capable of hybridizing to the first high throughput sequencing primer binding site sequence; v) a second high throughput sequencing primer capable of hybridizing to the second high throughput sequencing primer binding site sequence and vi) at least one dideoxynucleotide; b) hybridizing the first high throughput sequencing primer to the first high throughput sequencing primer binding site to generate an amplified first read sequence; c) terminating the first read sequence amplification with the dideoxynucleotide; and d) hybridizing the second high throughput sequencing primer to the second high throughput sequencing primer binding site to generate an amplified second read sequence. In one embodiment, each of the at least one nucleic acid fragment sequences is derived from a single genome. In one embodiment, each of the at least one nucleic acid fragment sequences is derived from a single library. In one embodiment, each of the at least one nucleic acid fragment sequences is derived from a single library insert sequence. In one embodiment, the first nucleic acid fragment sequence comprises a first read pair sequence. In one embodiment, the second nucleic acid fragment sequence comprises a second read pair sequence. In one embodiment, the bead is an emulsion polymerase chain reaction bead. In one embodiment, the at least one dideoxynucleotide comprises a cytosine. In one embodiment, the at least one dideoxynucleotide comprises a thymidine. In one embodiment, the at least one dideoxynucleotide comprises a guanosine. In one embodiment, the at least one dideoxynucleotide comprises an adenine. In one embodiment, the first and second high throughput sequencing primers are 454 sequencing primers. In one embodiment, the first and second high throughput sequencing primers are Illumina sequencing primers. In one embodiment, the first and second high throughput sequencing primers are SOLiD sequencing primers. In one embodiment, the first and second high throughput sequencing primers are ion semiconductor sequencing primers. In one embodiment, the method further comprises a single reaction mixture.

In one embodiment, the present invention contemplates a method, comprising: a) providing; i) a composition comprising a bead coated with at least one linker nucleic acid sequence ligated to at least one nucleic acid fragment sequence; ii) a first high throughput sequencing primer binding site sequence ligated to a first nucleic acid fragment sequence of the at least one nucleic acid fragment sequences; iii) a second high throughput sequencing primer binding site sequence ligated to a second nucleic acid fragment sequence of the at least one nucleic acid fragment sequences; iv) a first high throughput sequencing primer capable of hybridizing to the first high throughput sequencing primer binding site sequence; v) a second high throughput sequencing primer capable of hybridizing to the second high throughput sequencing primer binding site sequence and vi) a deoxynuclease enzyme; b) hybridizing the first high throughput sequencing primer to the first high throughput sequencing primer binding site to generate a first amplified read sequence; c) cleaving the first amplified read sequence with the deoxynuclease; d) hybridizing the second high throughput sequencing primer to the second high throughput sequencing primer binding site to generate an amplified second read sequence. In one embodiment, each of the at least one nucleic acid fragment sequences is derived from a single genome. In one embodiment, each of the at least one nucleic acid fragment sequences is derived from a single library. In one embodiment, each of the at least one nucleic acid fragment sequences is derived from a single library insert sequence. In one embodiment, the first nucleic acid fragment sequence comprises a first read pair sequence. In one embodiment, the second nucleic acid fragment sequence comprises a second read pair sequence. In one embodiment, the bead comprises an emulsion polymerase chain reaction bead. In one embodiment, the first and second high throughput sequencing primers are 454 sequencing primers. In one embodiment, the first and second high throughput sequencing primers are Illumina sequencing primers. In one embodiment, the first and second high throughput sequencing primers are SOLiD sequencing primers. In one embodiment, the first and second high throughput sequencing primers are ion semiconductor sequencing primers. In one embodiment, the method further comprises a single reaction mixture.

In one embodiment, the present invention contemplates a composition comprising a bead attached to at least one second high throughput sequencing primer ligated to a thioester linker sequence, wherein the thioester linker sequence is ligated to at least one nucleic acid fragment sequence. In one embodiment, the at least one nucleic acid fragment sequence is ligated to at least one high throughput sequencing primer site. In one embodiment, the at least one nucleic acid fragment sequences are derived from a single genome. In one embodiment, the at least one nucleic acid fragment sequences are derived from a single library. In one embodiment, the at least one nucleic acid fragment sequences are derived from a single library insert sequence. In one embodiment, the thioester linker sequence ranges between one and four adjacent thioester groups. In one embodiment, a first nucleic acid fragment sequence of the at least one nucleic acid fragment sequences comprises a first read pair sequence. In one embodiment, a second nucleic acid fragment sequence of the at least one nucleic acid fragment sequences comprises a second read pair sequence. In one embodiment, the first high throughput sequencing primer binding site is hybridized to a first high throughput sequencing primer. In one embodiment, the composition further comprises at least one amplified read sequence. In one embodiment, the first and second high throughput sequencing primers are 454 sequencing primers. In one embodiment, the first and second high throughput sequencing primers are Illumina sequencing primers. In one embodiment, the first and second high throughput sequencing primers are SOLiD sequencing primers. In one embodiment, the first and second high throughput sequencing primers are ion semiconductor sequencing primers.

In one embodiment, the present invention contemplates a method, comprising: a) providing; i) a bead attached to at least one second high throughput sequencing primer ligated to a thioester linker sequence, wherein the thioester linker sequence is ligated to at least one nucleic acid fragment sequence; ii) a first high throughput sequencing primer binding site sequence ligated to the at least nucleic acid fragment sequence; iii) a first high throughput sequencing primer capable of hybridizing to the first high throughput sequencing primer binding site sequence; vi) at least one dideoxynucleotide; and v) an exonuclease enzyme; b) hybridizing the first high throughput sequencing primer to the first high throughput sequencing primer binding site to generate an amplified first read sequence (Read 1); c) terminating the first read sequence amplification with the dideoxynucleotide; d) digesting a first portion the nucleic acid fragment sequence with the exonuclease, such that a second portion of the nucleic acid fragment remains; and e) extending the second portion of the nucleic acid fragment with the second high throughput sequencing primer to generate an amplified second read sequence (Read 2). In one embodiment, the at least one nucleic acid fragment sequences are derived from a single genome. In one embodiment, the at least one nucleic acid fragment sequences are derived from a single library. In one embodiment, the at least one nucleic acid fragment sequences are derived from a single library insert sequence. In one embodiment, the thioester linker sequence ranges between one and four adjacent thioester groups. In one embodiment, a first nucleic acid fragment sequence of the at least one nucleic acid fragment sequences comprises a first read pair sequence. In one embodiment, a second nucleic acid fragment sequence of the at least one nucleic acid fragment sequences comprises a second read pair sequence. In one embodiment, the method further comprises performing emulsion polymerase chain reaction on the bead. In one embodiment, the at least one dideoxynucleotide comprises a cytosine. In one embodiment, the at least one dideoxynucleotide comprises a thymidine. In one embodiment, the at least one dideoxynucleotide comprises a guanosine. In one embodiment, the at least one dideoxynucleotide comprises an adenine. In one embodiment, the first and second high throughput sequencing primers are 454 sequencing primers. In one embodiment, the first and second high throughput sequencing primers are Illumina sequencing primers. In one embodiment, the first and second high throughput sequencing primers are SOLiD sequencing primers. In one embodiment, the first and second high throughput sequencing primers are ion semiconductor sequencing primers. In one embodiment, the method is performed in a single reaction mixture.

In one embodiment, the present invention contemplates a composition comprising a bead attached to at least one second high throughput sequencing primer ligated to at least one ribonucleotide base linker, wherein the at least one ribonucleotide base linker is ligated to at least one nucleic acid fragment sequence. In one embodiment, the ribonucleotide base linker comprises between one and four ribonucleotide bases. In one embodiment, the ribonucleotide base is uracil. In one embodiment, the at least one nucleic acid fragment sequence is ligated to at least one high throughput sequencing primer site. In one embodiment, the at least one nucleic acid fragment sequences are derived from a single genome. In one embodiment, the at least one nucleic acid fragment sequences are derived from a single library. In one embodiment, the at least one nucleic acid fragment sequences are derived from a single library insert sequence. In one embodiment, a first nucleic acid fragment sequence of the at least one nucleic acid fragment sequences comprises a first read pair sequence. In one embodiment, a second nucleic acid fragment sequence of the at least one nucleic acid fragment sequences comprises a second read pair sequence. In one embodiment, the first high throughput sequencing primer binding site is hybridized to a first high throughput sequencing primer. In one embodiment, the composition further comprises at least one amplified read sequence. In one embodiment, the first and second high throughput sequencing primers are 454 sequencing primers. In one embodiment, the first and second high throughput sequencing primers are Illumina sequencing primers. In one embodiment, the first and second high throughput sequencing primers are SOLiD sequencing primers. In one embodiment, the first and second high throughput sequencing primers are ion semiconductor sequencing primers.

In one embodiment, the present invention contemplates a method, comprising: a) providing; i) a bead attached to at least one second high throughput sequencing primer ligated to a ribonucleotide base linker, wherein the ribonucleotide base linker is ligated to at least one nucleic acid fragment sequence; ii) a first high throughput sequencing primer binding site sequence ligated to the at least nucleic acid fragment sequence; iii) a first high throughput sequencing primer capable of hybridizing to the first high throughput sequencing primer binding site sequence; iv) a ribonuclease enzyme capable of creating a single strand nick adjacent to the ribonucleotide base linker; and v) a polymerase enzyme capable of attaching to the nick; b) hybridizing the first high throughput sequencing primer to the first high throughput sequencing primer binding site to generate an amplified first read sequence (Read 1); c) contacting the ribonucleotide base linker with the ribonuclease enzyme, wherein the nick is created; and d) attaching the polymerase to the nick and the second high throughput sequencing primer under conditions that generate an amplified second read sequence (Read 2). In one embodiment, the at least one ribonucleotide base linker ranges between one and four ribonucleotide bases. In one embodiment, the ribonucleotide base is uracil. In one embodiment, the ribonuclease enzyme is RNase H2. In one embodiment, the polymerase is bst polymerase. In one embodiment, the at least one nucleic acid fragment sequences are derived from a single genome. In one embodiment, the at least one nucleic acid fragment sequences are derived from a single library. In one embodiment, the at least one nucleic acid fragment sequences are derived from a single library insert sequence. In one embodiment, a first nucleic acid fragment sequence of the at least one nucleic acid fragment sequences comprises a first read pair sequence. In one embodiment, a second nucleic acid fragment sequence of the at least one nucleic acid fragment sequences comprises a second read pair sequence. In one embodiment, the method further comprises performing emulsion polymerase chain reaction on the bead. In one embodiment, the first and second high throughput sequencing primers are 454 sequencing primers. In one embodiment, the first and second high throughput sequencing primers are Illumina sequencing primers. In one embodiment, the first and second high throughput sequencing primers are SOLiD sequencing primers. In one embodiment, the first and second high throughput sequencing primers are ion semiconductor sequencing primers. In one embodiment, the method is performed in a single reaction mixture.

In one embodiment, the present invention contemplates a composition comprising a bead coated with a plurality of streptavidin molecules, wherein the streptavidin molecules are bound to a plurality of biotin labeled random primer sequences and wherein said random primer sequences are hybridized to a plurality of nucleic acid fragment sequences. In one embodiment, the plurality of nucleic acid fragment sequences are derived from a single genome. In one embodiment, the plurality of nucleic acids are derived from a single library. In one embodiment, the plurality of nucleic acid fragment sequences are derived from a single library insert sequence. In one embodiment, each of the plurality of nucleic acid fragments is ligated to a linker nucleic acid sequence. In one embodiment, the linker nucleic acid sequence comprises at least one high throughput sequencing primer binding site. In one embodiment, the at least one high throughput sequencing primer binding site is a first high throughput sequencing primer binding site. In one embodiment, the at least one high throughput sequencing primer binding site is a second high throughput sequencing primer binding site. In one embodiment, the composition further comprises a plurality of amplified nucleic acid fragment sequences. In one embodiment, a first nucleic acid fragment of the plurality of nucleic acid fragment sequences comprises a first read pair sequence. In one embodiment, a second nucleic acid fragment of the plurality of nucleic acid fragment sequences comprises a second read pair sequence. In one embodiment, the nucleic acid fragment sequences are circularized. In one embodiment, the composition further comprises a plurality of amplified read sequences. 145. In one embodiment, random primer is a hexamer. In one embodiment, random primer is a heptamer. In one embodiment, random primer is an octomer. In one embodiment, the random primer is a nonomer. In one embodiment, the random primer is NNNNNN, NNNNNNN, NNNNNNNN, or NNNNNNNNN wherein N is a nucleoside. In one embodiment, the nucleoside may include but is not limited to adenosine (A), guanosine (G), thymidine (T) and/or cytosine (C). In one embodiment, the random primer is AGTCCT. In one embodiment, the random primer is TCCTGAG. In one embodiment, the random primer is TGATCCAT. In one embodiment, the random primer is CGTACGTCT.

In one embodiment, the present invention contemplates a method, comprising: a) providing; i) a bead coated with a plurality of streptavidin molecules; ii) a plurality of biotin labeled random primer sequences; and iii) a plurality of circularized nucleic acid fragments; b) binding the biotin labeled random primer sequences to the streptavidin coated bead; and c) annealing the plurality of circularized nucleic acid fragments to the random primer sequences under conditions that generate an amplified plurality of nucleic acid fragments. In one embodiment, the plurality of circularized nucleic acid fragments are derived from a single genome. In one embodiment, the plurality of circularized nucleic acid fragments are derived from a single library. In one embodiment, the plurality of circularized nucleic acid fragments are derived from a single library insert sequence. In one embodiment, each of the amplified plurality of nucleic acid fragments is attached to the bead. In one embodiment, each of the plurality of nucleic acid fragments comprise a linker nucleic acid sequence. In one embodiment, the linker nucleic acid sequence comprises at least one high throughput sequencing primer binding site. In one embodiment, the at least one high throughput sequencing primer binding site is a first high throughput sequencing primer binding site. In one embodiment, the at least one high throughput sequencing primer binding site is a second high throughput sequencing primer binding site. In one embodiment, the amplified nucleic acid fragment comprises a first read pair sequence. In one embodiment, the amplified nucleic acid fragment sequence comprises a second read pair sequence. In one embodiment, the amplified nucleic acid fragment sequence comprises the first read pair sequence and the second read pair sequence. In one embodiment, the method further provides a first high throughput sequencing primer. In one embodiment, The method of further provides a second high throughput sequencing primer. In one embodiment, the method further comprises amplifying the first read pair sequence with the first high throughput sequencing primer, thereby generating a first read sequence. In one embodiment, the method further comprises amplifying the second read pair sequence with the second high throughput sequencing primer, thereby generating a second read sequence. In one embodiment, the first and second high throughput sequencing primers are 454 sequencing primers. In one embodiment, the first and second high throughput sequencing primers are Illumina sequencing primers. In one embodiment, the first and second high throughput sequencing primers are SOLiD sequencing primers. In one embodiment, the first and second high throughput sequencing primers are ion semiconductor sequencing primers. In one embodiment, the composition further comprises a plurality of amplified read sequences. In one embodiment, random primer is a hexamer. In one embodiment, random primer is a heptamer. In one embodiment, random primer is an octomer. In one embodiment, the random primer is a nonomer. In one embodiment, the random primer is NNNNNN, NNNNNNN, NNNNNNNN, or NNNNNNNNN wherein N is a nucleoside. In one embodiment, the nucleoside may include but is not limited to adenosine (A), guanosine (G), thymidine (T) and/or cytosine (C). In one embodiment, the random primer is AGTCCT. In one embodiment, the random primer is TCCTGAG. In one embodiment, the random primer is TGATCCAT. In one embodiment, the random primer is CGTACGTCT.

In one embodiment, the present invention contemplates a kit comprising: a) a first container comprising a solid substrate capable of attaching at least one nucleic acid fragment sequence by a linker sequence, wherein the nucleic acid fragment sequence comprises a plurality of subsequences; b) a second container comprising a first high throughput sequencing primer capable of amplifying a first subsequence of the plurality of subsequences; c) a third container comprising a second high throughput sequencing primer capable of amplifying a second subsequence of the plurality of subsequences and d) instructions for co-amplifying said first and second subsequences with said first and second high throughput sequencing primers in a single reaction mixture. In one embodiment, the solid substrate comprises a bead. In one embodiment, the solid substrate comprises a microwell. In one embodiment, the instructions provide attaching the plurality of subsequences to said solid substrate as separate sequences. In one embodiment, the instructions provide attaching the plurality of subsequences to said solid substrates as a single sequence. In one embodiment, the at least one nucleic acid fragment is derived from a single genome. In one embodiment, the at least one nucleic acid fragment is derived from a single library. In one embodiment, the at least one nucleic acid fragment is derived from a single library insert sequence. In one embodiment, the plurality of subsequences comprises a first read pair sequence. In one embodiment, the plurality of subsequences comprises a second read pair. In one embodiment, the first read pair sequence is ligated to a first high throughput sequencing primer binding site. In one embodiment, the second read pair sequence is ligated to a second high throughput sequencing primer binding site. In one embodiment, the instructions provide amplifying the first read pair sequence with the first high throughput sequencing primer. In one embodiment, the instructions provide removing the first high throughput sequencing primer from the first amplified read pair. In one embodiment, the instructions provide amplifying the second read pair sequence with the second high throughput sequencing primer. In one embodiment, the instructions provide removing the second high throughput sequencing primer from the second read pair. In one embodiment, the kit further comprises a third container comprising at least one enzyme. In one embodiment, the enzyme may including but not limited to an exonuclease enzyme (e.g., exonuclease III) or a ribonuclease enzyme. In one embodiment, the first and second high throughput sequencing primers are 454 sequencing primers. In one embodiment, the first and second high throughput sequencing primers are Illumina sequencing primers. In one embodiment, the first and second high throughput sequencing primers are SOLiD sequencing primers. In one embodiment, the first and second high throughput sequencing primers are ion semiconductor sequencing primers. In one embodiment, the instructions provide performing the simultaneous amplification in a single reaction mixture. In one embodiment, the linker sequence comprises a nucleic acid sequence. In one embodiment, the linker sequence comprises a plurality of thioester linkages. In one embodiment, the linker sequence comprises a plurality of ribonucleic acid bases. In one embodiment, the ribonucleic acid bases are uracil.

In one embodiment, the present invention contemplates a method, comprising: a) providing; i) a bead coated with a plurality of streptavidin molecules; ii) a plurality of biotin labeled random primer sequences; and iii) a plurality of circularized nucleic acid fragments; and b) annealing the plurality of circularized nucleic acid fragments to the random primer sequences under conditions that generate an amplified plurality of biotin-labeled nucleic acid fragments. In one embodiment, the method further comprises step c) binding the biotin labeled random primer sequences to the streptavidin coated bead. In one embodiment, the plurality of circularized nucleic acid fragments are derived from a single genome. In one embodiment, the plurality of circularized nucleic acid fragments are derived from a single library. In one embodiment, the plurality of circularized nucleic acid fragments are derived from a single library insert sequence. In one embodiment, each of the amplified plurality of nucleic acid fragments is attached to the bead. In one embodiment, each of the plurality of nucleic acid fragments comprise a linker nucleic acid sequence. In one embodiment, the linker nucleic acid sequence comprises at least one high throughput sequencing primer binding site. In one embodiment, the at least one high throughput sequencing primer binding site is a first high throughput sequencing primer binding site. In one embodiment, the at least one high throughput sequencing primer binding site is a second high throughput sequencing primer binding site. In one embodiment, the amplified nucleic acid fragment comprises a first read pair sequence. In one embodiment, the amplified nucleic acid fragment sequence comprises a second read pair sequence. In one embodiment, the amplified nucleic acid fragment sequence comprises the first read pair sequence and the second read pair sequence. In one embodiment, the method further provides a first high throughput sequencing primer. In one embodiment, The method of further provides a second high throughput sequencing primer. In one embodiment, the method further comprises amplifying the first read pair sequence with the first high throughput sequencing primer, thereby generating a first read sequence. In one embodiment, the method further comprises amplifying the second read pair sequence with the second high throughput sequencing primer, thereby generating a second read sequence. In one embodiment, the first and second high throughput sequencing primers are 454 sequencing primers. In one embodiment, the first and second high throughput sequencing primers are Illumina sequencing primers. In one embodiment, the first and second high throughput sequencing primers are SOLiD sequencing primers. In one embodiment, the first and second high throughput sequencing primers are ion semiconductor sequencing primers. In one embodiment, the composition further comprises a plurality of amplified read sequences. In one embodiment, random primer is a hexamer. In one embodiment, random primer is a heptamer. In one embodiment, random primer is an octomer. In one embodiment, the random primer is a nonomer. In one embodiment, the random primer is NNNNNN, NNNNNNN, NNNNNNNN, or NNNNNNNNN wherein N is a nucleoside. In one embodiment, the nucleoside may include but is not limited to adenosine (A), guanosine (G), thymidine (T) and/or cytosine (C). In one embodiment, the random primer is AGTCCT. In one embodiment, the random primer is TCCTGAG. In one embodiment, the random primer is TGATCCAT. In one embodiment, the random primer is CGTACGTCT.

DEFINITIONS

The term, "random primer" refers to any nucleotide sequence ranging between approximately six-nine nucleotides (i.e., for example, a hexamer, a heptamer, an octomer, and/or a nonomer) that are complementary to any portion of a template nucleic acid sequence.

The term, "universal primer" refers to any oligonucleotide used as a primer in DNA sequencing reactions that are specific for plasmid sequences (e.g., for example, pUC vectors, which in turn come from pBR322) flanking a cloned DNA insert. For example, nucleic acid sequences from T3, T7, or SP6 promoters are commonly used as flanking sequences, primers annealing to them can be used to obtain sequences of inserts cloned in a variety of vectors.

The term "dideoxynucleotides, or ddNTPs" refer to nucleotides lacking a 3'-hydroxyl (—OH) group on their deoxyribose sugar. Since deoxyribose already lacks a 2'-OH, dideoxyribose lacks hydroxyl groups at both its 2' and 3' carbons. The lack of this hydroxyl group means that, after being added by a DNA polymerase to a growing nucleotide chain, no further nucleotides can be added as no phosphodiester bond can be created based on the fact that deoxyribonucleoside triphosphates (which are the building blocks of DNA) allow DNA chain synthesis to occur through a condensation reaction between the 5' phosphate (following the cleavage of pyrophosphate) of the current nucleotide with the 3' hydroxyl group of the previous nucleotide. The dideoxyribonucleotides do not have a 3' hydroxyl group, hence no further chain elongation can occur once this dideoxynucleotide is on the chain. This can lead to the termination of the DNA sequence.

The term "linker" or "attachment feature" refers to any molecule that couples at least two different molecules together. For example, a nucleic acid sequence, a thioester sequence or a ribonucleic acid sequence may serve as a linker or attachment feature. Alternatively, non-nucleic acid compound are also contemplated as attachment features such as streptavidin and/or biotin.

The term "barcode" as used herein, refers to any unique, non-naturally occurring, nucleic acid sequence that may be used to identify the originating genome of a nucleic acid fragment. Such barcodes may be sequences including but not limited to, TTGAGCCT, AGTTGCTT, CCAGTTAG, ACCAACTG, GTATAACA or CAGGAGCC. Although it is not necessary to understand the mechanism of an invention, it is believed that the barcode sequence provides that the second single stranded bead product constitutes a high-quality individual read of a barcode associated with a sample such that multiple beads with different samples can be sequenced together.

The term "ligation" and "ligating" as used herein, refers to any method that forms two covalent phosphodiester bonds between 3' hydroxyl ends of one nucleotide, ("acceptor") with the 5' phosphate end of another ("donor"). ATP is required for the ligase reaction, which proceeds in three steps: (1) adenylation (addition of AMP) of a residue in the active center of the enzyme, pyrophosphate is released; (2) transfer of the AMP to the 5' phosphate of the so-called donor, formation of a pyrophosphate bond; (3) formation of a phosphodiester bond between the 5' phosphate of the donor and the 3' hydroxyl of the acceptor. For example, ligation may be easily performed by contacting nucleic acids with a DNA ligase enzyme (i.e., for example, (EC 6.5.1.1).

The term "solid support" or "solid substrate", as used herein refers to any material configured to chemically bond (i.e., for example, covalently and/or non-covalently) with a nucleic acid including but not limited to plastic, latex, glass, metal (i.e., for example, a magnetized metal), nylon, nitrocellulose, quartz, silicon, or ceramic. For example, a solid support may be roughly spherical (i.e., for example, a bead). Alternatively, a solid support/substrate may comprise a standard laboratory container such as a microwell plate or surface.

The term "clone library", as used herein, refers to any population of organisms, each of which carries a DNA molecule inserted into a cloning vector, or alternatively, to a collection of all of the cloned vector molecules representing a specific genome.

The term "vector", as used herein refers to any plasmid or bacteriophage that has been used to infect a microorganisms, comprising at least one nucleotide sequence of interest that is preserved as an insert.

The term "library", as used herein refers to a clone library, or alternatively, a library of genome-derived sequences carrying vector sequences. The library may also have sequences allowing amplification of the "library" by the polymerase chain reaction or other in vitro amplification methods well known to those skilled in the art. The library may also have sequences that are compatible with next-generation high throughput sequencers including but not limited to Illumina adapter pair sequences.

The term "read pair" as used herein refers to two nucleic acid sequences within a library insert sequence that are selected for high throughput sequencing. Each nucleic acid sequence of the read pair may be referred to as a "first read pair sequence" and a "second read pair sequence". Once the read pair is sequenced by a high throughput sequencing platform, the sequenced read pair may be referred to as "a first read" and "a second read".

The term "short read" as used herein refers to any nucleic acid sequence of ranging between approximately 25-500 base pairs, but preferably ranging between 50-300 base pairs, but even more preferably ranging between approximately 75-150 base pairs, but most preferably approximately 100 base pairs that is compatible with a high throughput sequencer.

The term "next-generation sequencing platform" as used herein, refers to any nucleic acid sequencing device that utilizes massively parallel technology. For example, such a platform may include, but is not limited to, Illumina sequencing platforms.

The term "high throughput sequencer adapter pair" refers to a specific nucleic acid pair that provides compatibility with a massively parallel sequencing platform (i.e., for example, Illumina sequencer adapter pairs). For example, an adapter pair may comprise the hybridization between a high throughput sequencing primer that is complementary to a high throughput sequencing primer binding site.

The term "ion semiconductor sequencing platform" refers to any device and/or method that detects the production of hydrogen ions during a chemical condensation reaction. The device and/or method quantitates the production of hydrogen ions by changes in the pH of a mixture and/or solution. For example, nucleic acids may be sequenced by measuring pH fluctuations in a mixture during amplification of a nucleic acid sequence.

The term "genome" as used herein, refers to a complete collection of genes representing a specific organism. For example, the genome may represent a microbial genome or a mammalian genome.

The term "coverage" as used herein, refers to an average number of reads representing a given nucleotide in the reconstructed sequence. It can be calculated from the length of the original genome (G), the number of reads (N), and the average read length (L) as NL/G. For example, a hypothetical genome with 2,000 base pairs reconstructed from 8 reads with an average length of 500 nucleotides will have 2× redundancy. This parameter also enables one to estimate other quantities, such as the percentage of the genome covered by reads (the coverage). A high coverage in shotgun sequencing is desired because it can overcome errors in base calling and assembly. The subject of DNA sequencing theory addresses the relationships of such quantities. Alternatively, the term "coverage" may refer to the average number of genome fragments present in a library covering a given nucleotide in the underlying genome.

The term "chain termination" as used herein, refers to any chemical reaction leading to the destruction of a reactive intermediate in a chain propagation step in the course of a polymerization, effectively bringing it to a halt. For example, chain termination may be used in the sequencing of nucleic acid polymers.

The term "bridge amplification' as used herein refers to any polymerase chain reaction that allows the generation of in situ copies of a specific DNA molecule on an oligo-decorated solid support. For example, bridge amplification is performed to produce DNA molecules that are compatible with an Illumina sequencing techniques.

The term "DNA sequencing" as used herein, refers to any methods for determining the order of the nucleotide bases—adenine, guanine, cytosine, and thymine—in a molecule of DNA.

The term "derived from" as used herein, refers to the source of a compound or sequence. In one respect, a compound or sequence may be derived from an organism or particular species. In another respect, a compound or sequence may be derived from a larger complex or sequence.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that some trace impurities may remain.

The term "label" or "detectable label" are used herein, to refer to any composition detectable by spectroscopic, photochemical, biochemical, immunochemical, electrical, optical or chemical means. A label may be a nucleic acid barcode label, where the label is identified by nucleic acid sequencing, or a universal primer. Such labels also include biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277, 437; 4,275,149; and 4,366,241 (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "genomic nucleic acid" as used herein refers to a naturally occurring nucleic acid sequence derived from a biological sample.

The term "an isolated nucleic acid", as used herein, refers to any nucleic acid molecule that has been removed from its natural state (e.g., removed from a cell and is, in a preferred embodiment, free of other genomic nucleic acid).

The term "labeled nucleic acid sequence", as used herein, refers to any nucleic acid molecule that is attached to a molecule that can be detected such that the nucleic acid is positively identified. For example, such labeled nucleic acid sequences may comprise, biotin, universal primers, nucleic acid barcodes, radioactive substituents, fluorescence substituents, phosphorescent substituents.

The term "attached" as used herein, refers to any interaction between a solid substrate (or bead) and a nucleic acid or a linker. Attachment may be reversible or irreversible. Such attachment includes, but is not limited to, covalent bonding, ionic bonding, Van der Waals forces or friction, and the like. Attachment may also comprise complementary hybridization, ligation or chemical bonding. A nucleic acid is also attached to a solid substrate (or bead) if it is impregnated, incorporated, coated, in suspension with, in solution with, mixed with, etc.

The term "portion" when used in reference to a nucleotide sequence refers to fragments of that nucleotide sequence. The fragments may range in size from 5 nucleotide residues to the entire nucleotide sequence minus one nucleic acid residue.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

An oligonucleotide sequence which is a "homolog" is defined herein as an oligonucleotide sequence which exhibits greater than or equal to 50% identity to a sequence, when sequences having a length of 100 bp or larger are compared.

Low stringency conditions comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent {50×Denhardt's contains per 500 ml: 5 g Ficoll (Type 400, Pharmacia), 5 g BSA (Fraction V; Sigma)} and 100 µg/ml denatured salmon sperm DNA followed by washing in a solution comprising 5×SSPE, 0.1% SDS at 42° C. when a probe of about 500 nucleotides in length. is employed. Numerous equivalent conditions may also be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) may also be used.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0 t$ or $R_0 t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" is used in reference to the "melting temperature." The melting temperature is the temperature at which a population of double-stranded nucleic acid molecules becomes half dissociated into single strands. As indicated by standard references, a simple estimate of the $T_m$ value may be calculated by the equation: $T_m=81.5+0.41$ (% G+C), when a nucleic acid is in aqueous solution at 1M NaCl. Anderson et al., "Quantitative Filter Hybridization" In: *Nucleic Acid Hybridization* (1985). More sophisticated computations take structural, as well as sequence characteristics, into account for the calculation of $T_m$.

As used herein the term "stringency" is used in reference to the conditions of temperature, ionic strength, and the presence of other compounds such as organic solvents, under which nucleic acid hybridizations are conducted. "Stringency" typically occurs in a range from about $T_m$ to about 20° C. to 25° C. below $T_m$. A "stringent hybridization" can be used to identify or detect identical polynucleotide sequences or to identify or detect similar or related polynucleotide sequences. For example, when fragments are employed in hybridization reactions under stringent conditions the hybridization of fragments which contain unique sequences (i.e., regions which are either non-homologous to or which contain less than about 50% homology or complementarity) are favored. Alternatively, when conditions of "weak" or "low" stringency are used hybridization may occur with nucleic acids that are derived from organisms that are genetically diverse (i.e., for example, the frequency of complementary sequences is usually low between such organisms).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Amplification" is defined as the production of additional copies of a nucleic acid sequence and is generally carried out either in vivo, i.e., for example by growing *E. coli* cells harboring recombinant (insert-containing) plasmid or fosmid vectors, or in vitro, i.e. for example using polymerase chain reaction. Dieffenbach C. W. and G. S. Dveksler (1995) In: *PCR Primer, a Laboratory Manual*, Cold Spring Harbor Press, Plainview, N.Y.

As used herein, the term "polymerase chain reaction" ("PCR") refers to the method of K. B. Mullis U.S. Pat. Nos. 4,683,195 and 4,683,202, herein incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. With PCR, it is also possible to amplify a complex mixture (library) of linear DNA molecules, provided they carry suitable universal sequences on either end such that universal PCR primers bind outside of the DNA molecules that are to be amplified.

As used herein, the term "primer" and "emulsion primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxy-ribonucleotide. The primer must be sufficiently long to prime the synthesis of extension products in the presence of the inducing agent. The exact lengths of the primers will depend on many factors, including temperature, source of primer and the use of the method.

The term "sequencing primer" as used herein, refers to a specific nucleotide sequence configured to initiate amplification for high throughput sequencer platforms, including but not limited to Illumina, SOLiD or 454.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "in operable combination" as used herein, refers to any linkage of nucleic acid sequences in such a manner that the nucleic acid molecules are capable of performed a coordinated function.

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

BRIEF DESCRIPTION OF THE FIGURES

FIG. 1 presents exemplary data showing proof of principle for co-amplification of paired read ends in a single reaction mixture that are compatible with a conventional 454 sequencing platform.

FIG. 2 presents exemplary data showing sequencing of an E. coli jumping library comprising 771 circularized jumping library insert sequences using the co-amplification method illustrated in FIG. 1. The data was collected in four (4) sets of runs: BOH276/277, GAM109/110, BOH 282/283, and GAM 115/116.

FIG. 3 presents one embodiment of a dual adaptor bead composition.

(FIG. 4A) a dideoxy nucleotide technique; and (FIG. 4B) a deoxynuclease technique.

FIG. 5 presents one embodiment of a bead composition capable of supporting an exonuclease method of co-amplification two read pairs of a nucleic acid fragment sequence.

FIG. 7 presents one embodiment of a bead composition capable of supporting a nick and proofread method of co-amplification of two read pairs of a nucleic acid fragment sequence.

DETAILED DESCRIPTION OF THE INVENTION

Figure 1A:
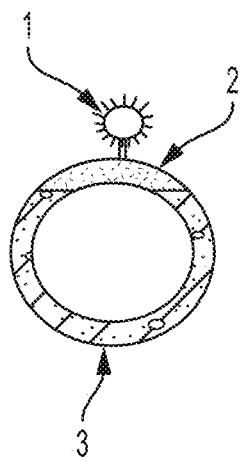
FIG. 1A: One embodiment of an approximate 100 bp circularized jumping library nucleic acid insert sequence (3) ligated with an approximate 3 kb biotinylated (1) linker sequence (2).

The present invention is related to genomic nucleotide sequencing. In particular, the invention describes a single reaction method to co-amplify multiple subsequences of a nucleic acid fragment sequence (i.e., for example, at least two read pairs from a single library insert sequence). Nucleic acid fragment sequences may include, but are not limited to, localizing library insert sequences and/or unique read pair sequences in specific orientations on a single emulsion polymerase chain reaction bead. Methods may include, but are not limited to, annealing, melting, digesting, and/or reannealing high throughput sequencing primers to high throughput sequencing primer binding sites. The compositions and methods disclosed herein contemplate sequencing complex genomes, amplified genomic regions, as well as detecting chromosomal structural rearrangements that are compatible with massively parallel high throughput sequencing platforms as well as ion semiconductor matching sequencing platforms (i.e., for example, Ion Torrent platforms).

I. Conventional Emulsion-Based Polymerase Chain Reaction (ePCR)

High throughput analysis of single molecules using emulsions has been previously reported. Tawfik et al., "Man-made cell-like compartments for molecular evolution" *Nat. Biotechnol.* 16:652-656 (1998). Recently, however, emulsion technology has been applied to next-generation sequencing. Shendure et al., "Accurate multiplex polony sequencing of an evolved bacterial genome" *Science* 309: 1728-1732 (2005). Emulsion technology that is compatible with next-generation sequencing usually involves a method for capturing the contents from the emulsion droplets. For example, one approach has been described to amplify single DNA molecules onto beads for detection and enumeration of genetic variation. (i.e., for example, BEAMing, for "beads, emulsion, amplification, and magnetics.") that has been used as one approach for emulsion PCR (ePCR). Dressman et al., "Transforming single DNA molecules into fluorescent magnetic particles for detection and enumeration of genetic variations" *Proc. Natl. Acad. Sci. USA* 100:8817-8822 (2003). DNA bound to beads generated during ePCR was capable of providing a template for high-throughput sequencing. Although it is not necessary to understand the mechanism of an invention, it is believed that ePCR can amplify a single molecule of DNA into many clonal molecules per bead. Due to that belief, a number of next-generation sequencing approaches utilize emulsions and beads for DNA amplification prior to high throughput sequencing. Shendure et al., "Next-generation DNA sequencing" *Nat. Biotechnol.* 26:1135-1145 (2008); Metzker, M. L., "Sequencing technologies—the next generation" *Nat. Rev. Genet* 11:31-46 (2010); Ansorge W. J., "Next-generation DNA sequencing techniques" *N. Biotechnol.* 25:195-203; Fullwood et al., "Next-generation DNA sequencing of paired-end tags (PET) for transcriptome and genome analyses" *Genome Res.* 19:521-532 (2009); and Mardis E. R., "Next-generation DNA sequencing methods" *Annu. Rev. Genomics Hum. Genet.* 9:387-402 (2008).

An alternative approach to amplify DNA for next-generation sequencing is the bridge amplification strategy (i.e., for example, Illumina-compatible amplification). Bing et al., promega.com/geneticidproc/ussymp7proc/0726. Bridge amplification uses a single aqueous compartment; however, the individual amplicons are constrained by primers bound to a solid phase that are extended and amplified. As the name implies, the extension product from one primer forms a bridge to the other primer. Pemov et al., "DNA analysis with multiplex micro array-enhanced PCR" *Nucleic Acids Res.* 33:e11 (2005).

Conventional ePCR has been applied to next-generation DNA sequencing. Porreca et al., "Polony DNA sequencing" *Curr. Protoc. Mol. Biol. Chapter* 7: Unit 7.8 (2006). Most of the next-generation sequencing approaches are restricted to short read lengths, such that optimization of human genome resequencing can be improved with either mate-paired or paired-end sequencing technologies. However, the construction of mate-paired libraries for next-generation sequencing is difficult and time-consuming (10). What is needed in the art are improved techniques for ePCR to overcome these limitations.

A. Dual Primer Emulsion Amplification

One recent improvements in emulsion. PCR has resulted in a report describing an approach called dual primer emulsion PCR (DPePCR). Xu et al., "Dual primer emulsion PCR for next-generation DNA sequencing" *BioTechniques* 48:409-412 (2010). DPePCR combines concepts from both emulsion PCR and bridge amplification for the generation of simple fragment libraries for paired-end next-generation sequencing. The DPePCR strategy can amplify short DNA fragments (less than ~300 bp, including genome fragment and primers) and enables sequencing of both ends of a DNA fragment. Although it is not necessary to understand the mechanism of an invention, it is believed that sequencing from both ends of a DNA fragment shortens library preparation time and increases the library complexity when compared with the construction of a mate-paired DNA library.

To perform DPePCR, both forward and reverse primers are attached to 1-μm beads. Additionally, since the amplicons are confined to the droplets, the amplification efficiency may be increased by including free primers in the aqueous phase. After ~120 PCR cycles, DPePCR has been reported to amplify a single DNA fragment in an emulsion drop. While the DNA is bound to the bead in a highly stable double-stranded state, one disadvantage of this method is that when under denaturing conditions, the double-stranded state immediately reforms, which inhibits the ability to sequence the DNA. To overcome this disadvantage, DPePCR must be performed with type II recognition enzyme sites (i.e., BceAI and AcuI) that are placed at the ends of the amplicons. Consequently, the DPePCR product is then be digested with restriction enzymes (i.e., BceAI and AcuI), and capping adaptors are ligated to the free end of the dsDNA before sequencing can begin. DPePCR products are sequenced using standard sequencing by ligation (SBL). The SBL sequencing strategy for DPePCR beads is identical to sequencing from standard ePCR beads. However, because of the presence of two paired-end fragments, both ends are sequenced independently, but in opposite directions. One strand is sequenced in the 3'→5' direction and the other strand is sequenced in the 5'→3' direction requiring a total of four different anchor primers.

II. Co-Amplification of Nucleic Acid Read Pairs

In one embodiment, the present invention contemplates co-amplifying nucleic acid sequences comprising annealing, melting and re-annealing different high throughput sequencing primer sequences to a plurality of read pair sequences.

Figure 1B:
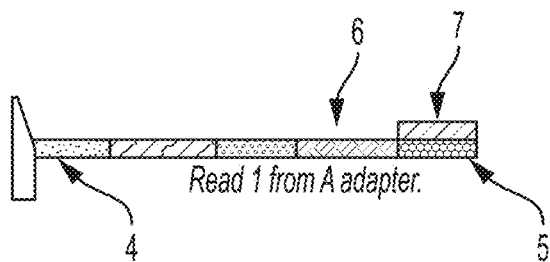
FIG. 1B: One embodiment of amplifying a first read pair (Read 1) with a first 454 sequencing primer annealed to 454 adapter A.
Figure 1C:
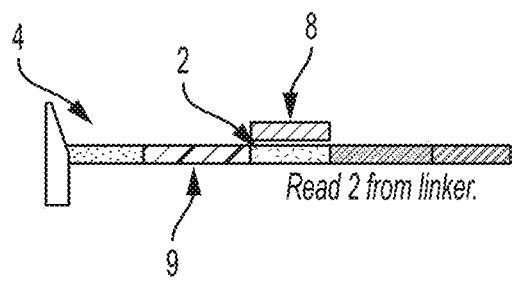
FIG. 1C: One embodiment of amplifying a second read pair (Read 2) with a second 454 primer annealed to the jumping library linker sequence.

For example, proof of principle was demonstrated using a 454-like biotinylated linker circularized jumping insert sequence library may be co-amplified using this approach, wherein a read pair sequence (3) is ligated to a linker sequence (2) attached to a biotin molecule (1). FIG. 1A. The read pair sequence (3) is then linearized and ligated to a 454 linker molecule (4). A first read sequence (6) of the read pair sequence (3) is amplified by a first 454 sequencing primer (7) hybridizing to a 454 Adapter A sequence (5). FIG. 1B. The first 454 sequencing primer (7) is then melted off the 454 Adapter A sequence (5) and a second 454 sequencing primer (8) is annealed to the linker sequence (2). A second read sequence (9) of the read pair sequence (3) is amplified by a second high throughput sequencing primer (8).

Figure 2A:
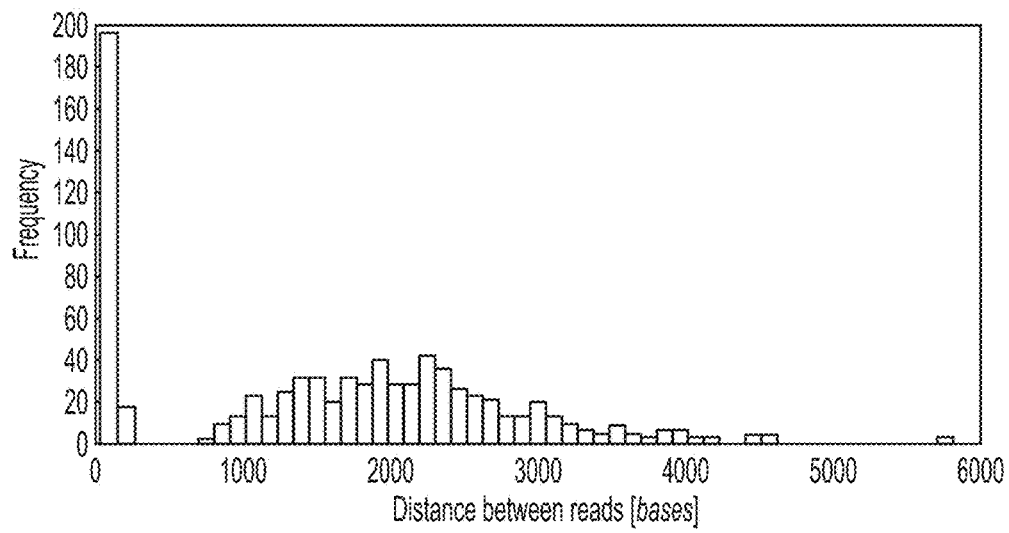
FIG. 2A: Frequency of distance between Read 1 and Read 2 of each jump insert sequence.
Figure 2B:
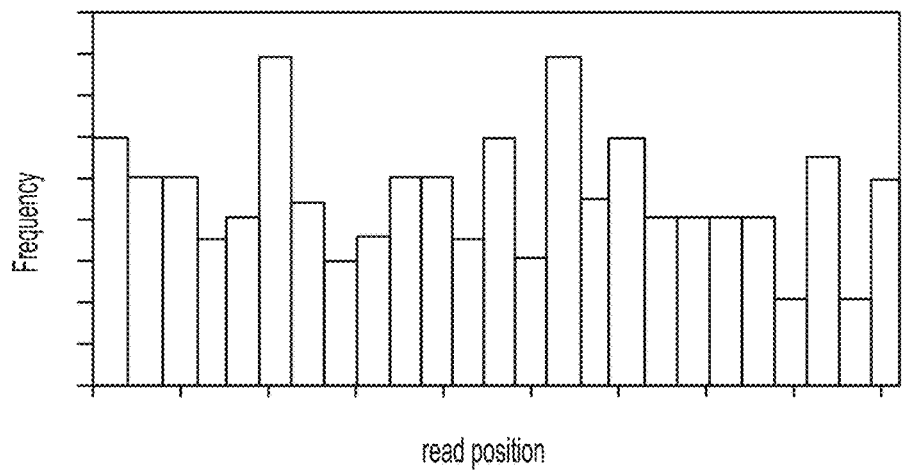
FIG. 2B: Frequency of read position of each jump sequence.

The data presented herein demonstrates the co-amplification of read pair sequences from an entire E. coli jumping library using a "melt and reanneal" technique. The data show that the distance between the two read sequences of each read pair sequence ranged from approximately 500 bps to 4750 bps, with a range of between approximately 2000-2500 bps having the highest frequency (e.g., 40 jumps out of 771 total jumps). FIG. 2A. The sequencing method also provided data showing the frequency of read position of each jump sequence. FIG. 2B.

This preliminary study was then adapted to implement various embodiments of the present invention wherein a first read sequence and a second read sequence of a single read pair sequence can be co-amplified in the same reaction mixture. In one embodiment, a first read pair sequence is ligated to a first high throughput sequencing primer site. In one embodiment, a second read pair sequence is ligated to a second high throughput sequencing primer site. In one embodiment, the present invention contemplates a method comprising annealing a first high throughput sequencing primer to the first read pair sequencing primer site wherein a first read is amplified (Read 1). In one embodiment, the first high throughput sequencing primer is removed from the first read pair by melting and/or enzymatic digestion. In one embodiment, the method further comprises annealing a second high throughput sequencing primer to the second read pair sequencing primer site wherein a second read is amplified (Read 2). In one embodiment, the method further comprises removing the second high throughput sequencing primer from the second read pair by melting and/or enzymatic digestion. In one embodiment, the digestion comprises an exonuclease enzyme (e.g., exonuclease III). In one embodiment, the digestion comprises a ribonuclease enzyme.

A. Dual Adapted Bead Method

Figure 3A:
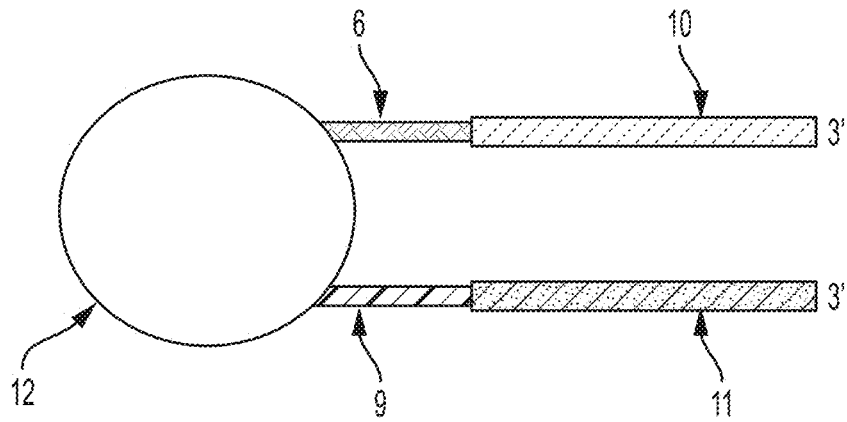
FIG. 3A: A dual adaptor bead composition comprising a first nucleic acid fragment sequence comprising a first high throughput sequencing primer binding site and a second nucleic acid fragment sequence comprising a second high throughput sequencing primer binding site.
Figure 3B:
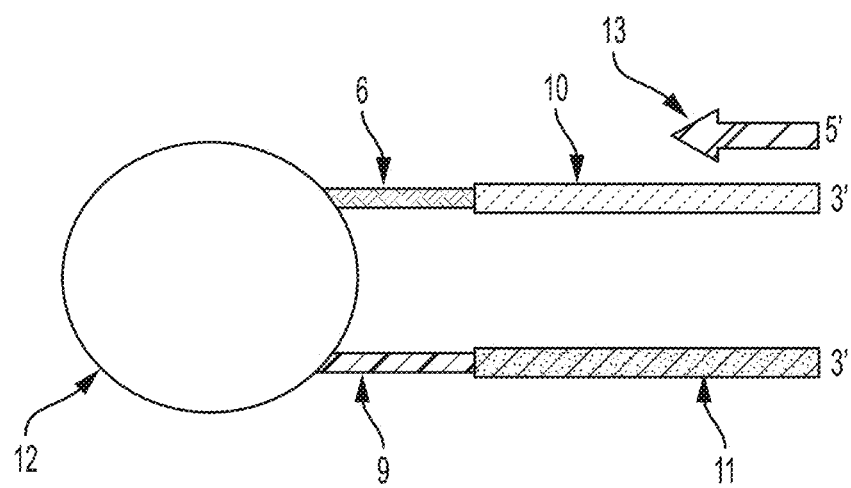
FIG. 3B: A dual adaptor bead composition as shown in FIG. 3A further comprising a first high throughput sequencing primer sequence.
Figure 3C:
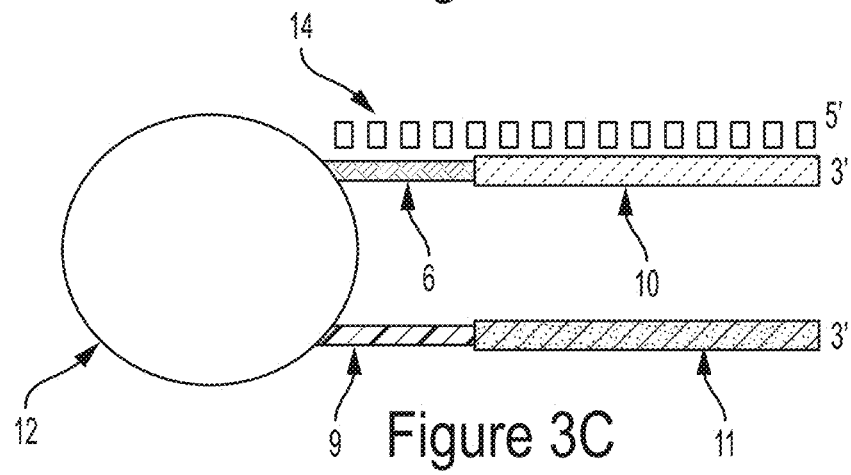
FIG. 3C: A dual adaptor bead composition as shown in FIG. 3A further comprising an amplified first read sequence.

In one embodiment, the present invention contemplates a dual adapted bead composition comprising a bead (12) coated with a plurality of linker nucleic acid sequences to which are attached a first read pair sequence (6) and/or a second read pair sequence (9). In one embodiment, the first read pair sequence is ligated to a first high throughput sequencing primer primer site sequence (10). In one embodiment, the second read pair sequence is ligated to a second high throughput sequencing primer binding site sequence (11). FIG. 3A. In one embodiment, the dual adapted bead composition further comprises at least one high throughput sequencing primer (13). FIG. 3B. In one embodiment, the dual adapted bead composition further comprises at least one amplified read sequence (14). FIG. 3C.

Figures 4A, 4B:
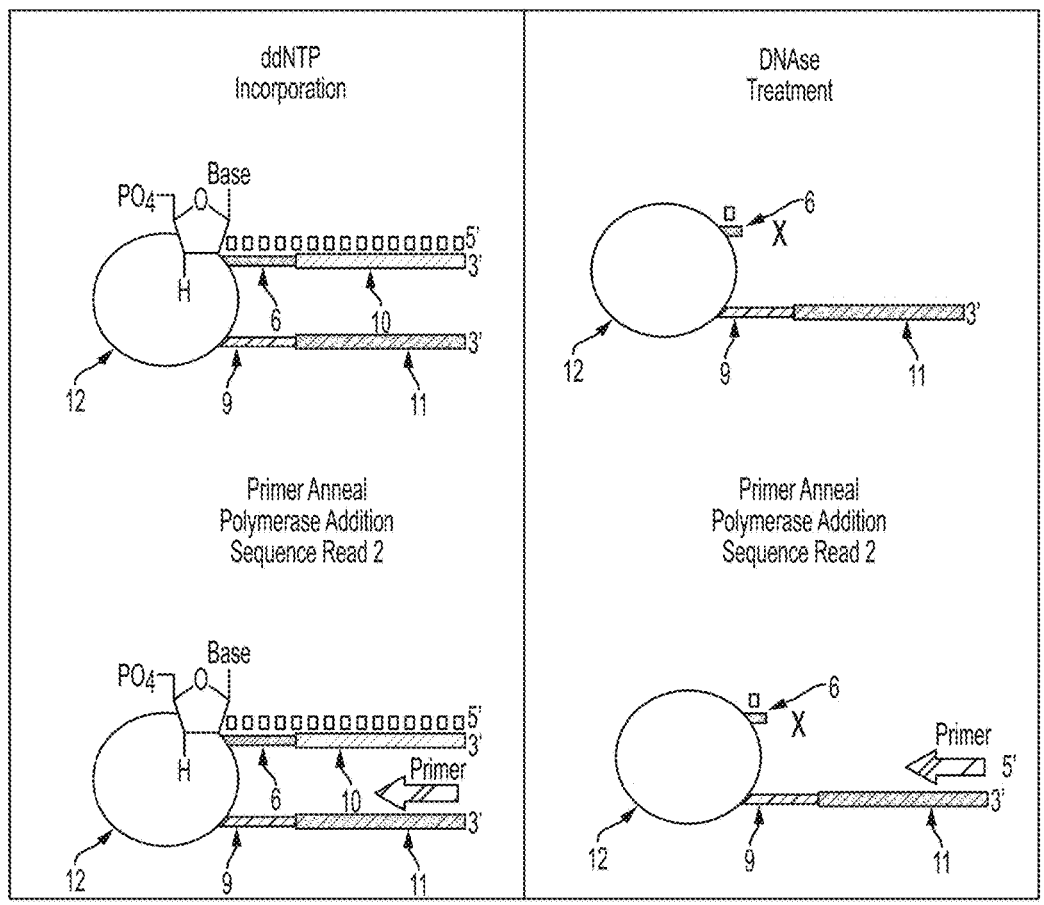
FIGS. 4A-4B show two embodiments of a method using a dual adaptor bead composition to co-amplify two read pairs of a nucleic acid fragment sequence using.

In one embodiment, the present invention contemplates a method comprising: providing; i) a dual adapted bead composition; ii) a first high throughput sequencing primer capable of hybridizing to the bead composition; iii) a second high throughput sequencing primer capable of hybridizing to the bead composition; and iv) at least one dideoxynucleotide; b) hybridizing the first high throughput sequencing primer to the bead composition under conditions that amplify at least one read sequence (Read 1); c) terminating the at least one read sequence amplification with the at least one dideoxynucleotide; and d) hybridizing the second high throughput sequencing primer to the bead composition under conditions that amplify a second read sequence (Read 2). FIG. 4A.

In one embodiment, the present invention contemplates a method comprising: providing; i) a dual adapted bead composition; ii) a first high throughput sequencing primer capable of hybridizing to the bead composition; iii) a second high throughput sequencing primer capable of hybridizing to the bead composition; and iv) a deoxynuclease enzyme; b) hybridizing the first sequencing primer to the bead composition under conditions that amplify at least one read sequence (Read 1); c) cleaving the at least one amplified read sequence from the bead composition with the deoxynuclease; and d) hybridizing the second sequencing primer to the bead composition under conditions that amplify a second read sequence (Read 2). FIG. 4B.

B. Exonuclease Method

Figure 5A:
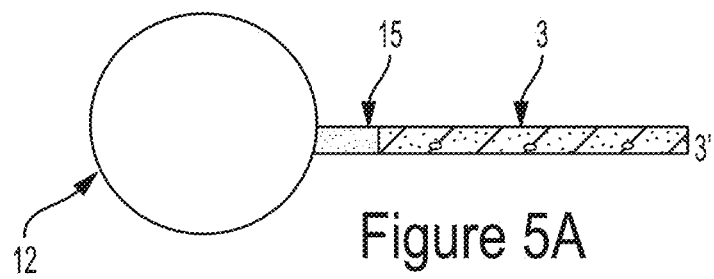
FIG. 5A: A bead composition attached to a nucleic acid fragment sequence using a thioester linkage sequence.
Figure 5B:
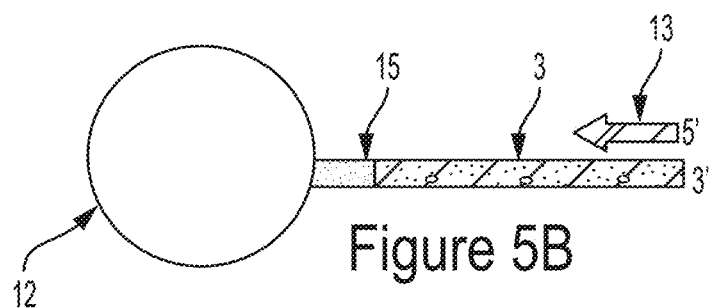
FIG. 5B: A bead composition as illustrated in FIG. 5A further comprising a hybridized first high throughput sequencing primer sequence.
Figure 5C:
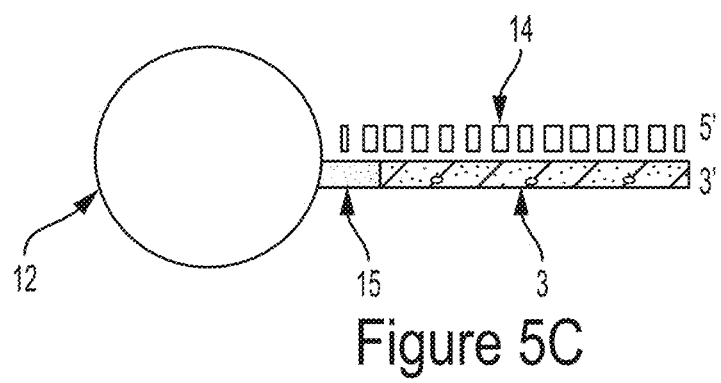
FIG. 5C: A bead composition as illustrated in FIG. 5A further comprising an amplified first read sequence.

In one embodiment, the present invention contemplates a composition comprising a bead (12) attached to at least one thioester linker sequence (15), wherein the linker sequence is ligated to at least one read pair sequence derived from a genome (e.g., a library insert sequence) (3). FIG. 5A. In one embodiment, the at least one read pair sequence (3) is ligated to a first high throughput sequencing primer binding site sequence. In one embodiment, the thioester linker sequence is ligated to a second high throughput sequencing primer binding site sequence. In one embodiment, the composition further comprises a first high throughput sequencing primer (13). FIG. 5B. In one embodiment, the composition further comprises an amplified read sequence (14). FIG. 5C. In one embodiment, the composition further comprises a second high throughput sequencing primer.

Figure 6:
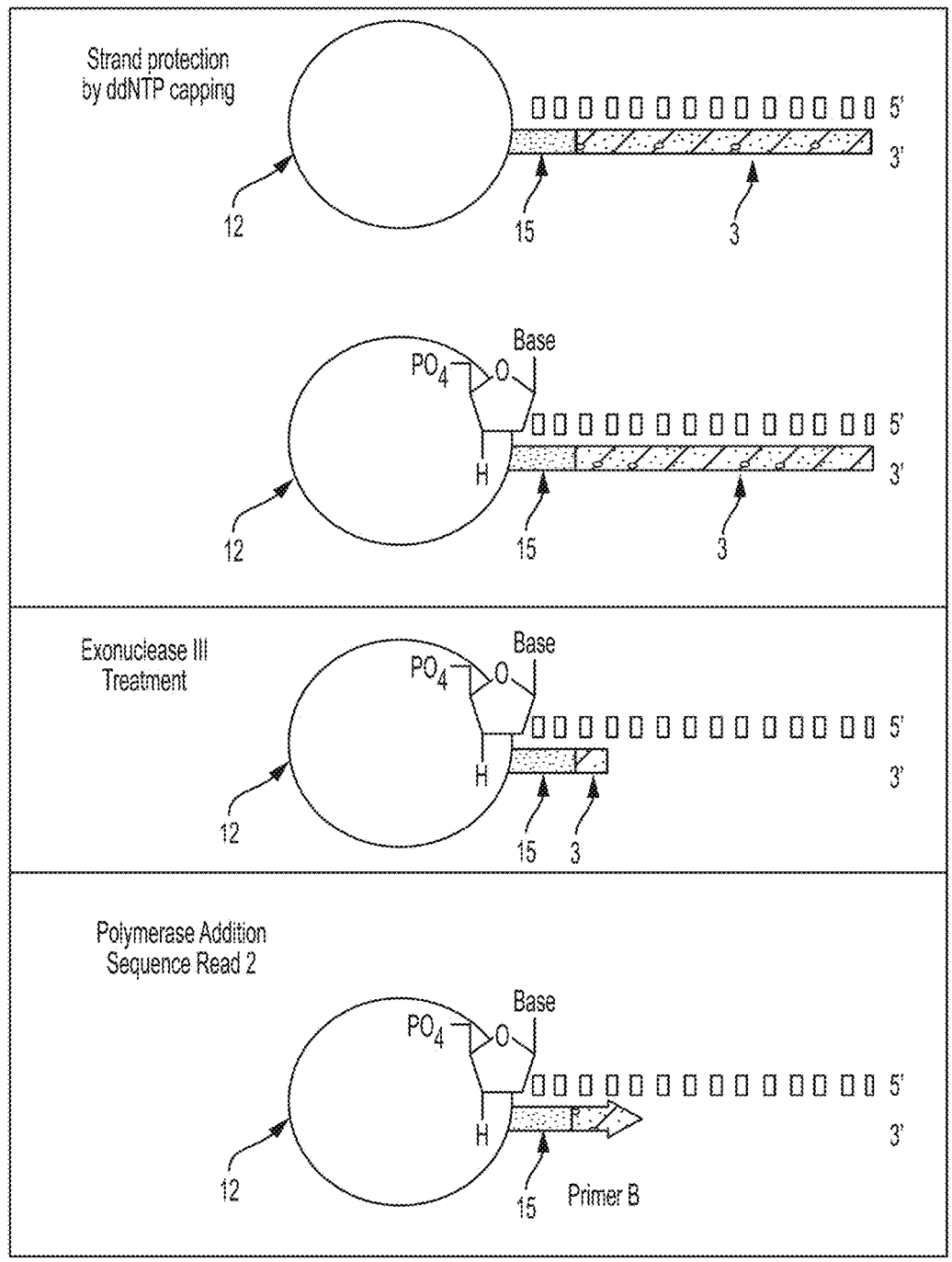
FIG. 6 presents one embodiment of an exonuclease digestion method to co-amplify a second read sequence subsequent to dideoxynucleotide capping of the amplified first read sequence and exonuclease digestion of the nucleic acid fragment sequence.

In one embodiment, the present invention contemplates a method comprising: providing; i) a bead (12) attached to at least one thioester linker (15), wherein the at least one linker sequence is ligated to at least one read pair sequence, where the at least one read pair sequence is derived from a genome (e.g., library insert sequence) (3); ii) a first high throughput sequencing primer capable of hybridizing to the at least one read pair sequence (3); iii) a second high throughput sequencing primer capable of hybridizing to the linker sequence; iv) a dideoxynucleotide; and iv) an exonuclease III enzyme; b) hybridizing the first high throughput sequencing primer to the read pair sequence under conditions that amplify a first read sequence (Read 1); c) terminating the first read sequence amplification with the dideoxynucleotide; d) digesting the insert sequence with the exonuclease III; and e) ligating the second sequencing primer to the linker sequence under conditions that amplify a second read sequence (Read 2). FIG. 6.

To describe a non-limiting embodiment in more detail, a primer/linker sequence may be attached to a bead. At the 3' end of the bead-attached oligo, there may be several (1-4) thioester bonds. Although it is not necessary to understand the mechanism of an invention, it is believed that the thioester bonds protect the bead end of the oligo from complete degradation and/or removal. Next, the primer/linker coated bead may be placed in an emulsion droplet, or in a microwell, with suitably linkered library nucleic acid molecules (i.e., for example, nucleic acid fragment library molecules or library nucleic acid insert molecules), polymerase and suitable primers. This mixture allows an emulsion PCR reaction to occur that results in an extension (i.e., amplification) of the on-bead oligo to produce a complement strand to the library nucleic acid molecules. Although it is not necessary to understand the mechanism of an invention, it is believed that the emulsion PCR happens many thousands of times on the surface of each bead and the mixing is such that a single clonal population of library inserts are cloned onto the surface of each bead. A sequencing primer may then be annealed to the library adapter sequence distal to the bead. Generally using a detector, a polymerase then mediates extension from the sequencing primer, thereby creating an amplified first read (Read 1). This process can either be: a) run the extension reaction to completion such that there are no more template bases left to make a complementary strand (i.e., the on-bead oligo is copied all the way back to the bead surface) or; b) run the extension reaction such that the amplification is at least extended beyond the thioester protected bases on the on-bead oligo, such that dideoxynucleotides may be added in combination with some other exonuclease blocking agent(s) that 'cap' the 3' end of the extended fragment. Then, an exonuclease enzyme may be used to directionally digest the on-bead oligo from the 3' end back toward the bead until such time that it reaches the thioester bonds. At this stage the exonuclease may be removed and a polymerase added. The polymerase should now be able to extend from the remaining on-bead oligo, which now serves as the sequencing primer, back in a 5'→3' direction creating an amplified second read sequence (Read 2) that is complementary to the amplified first read sequence (Read 1). Because the top strand is capped with a dideoxynucleotide, the top strand is not extended further.

C. Nick and Proofread Method

Figure 7A:
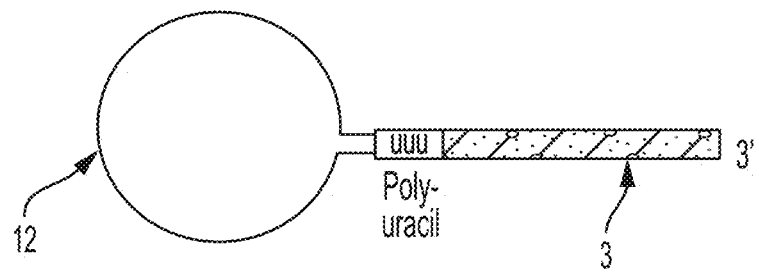
FIG. 7A: A bead composition attached to a nucleic acid fragment sequence using a polyuracil linker sequence.
Figure 7B:
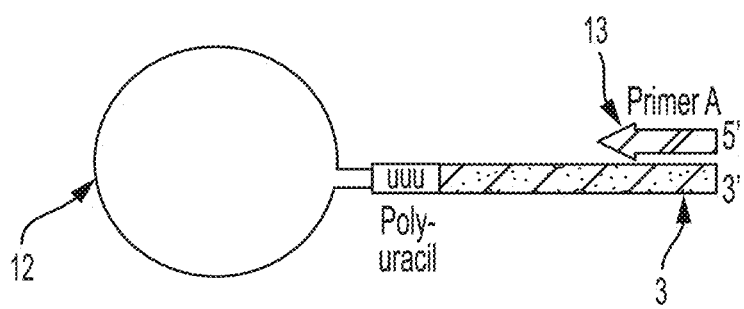
FIG. 7B: A bead composition as illustrated in FIG. 7A further comprising a hybridized first high throughput sequencing primer sequence.
Figure 7C:
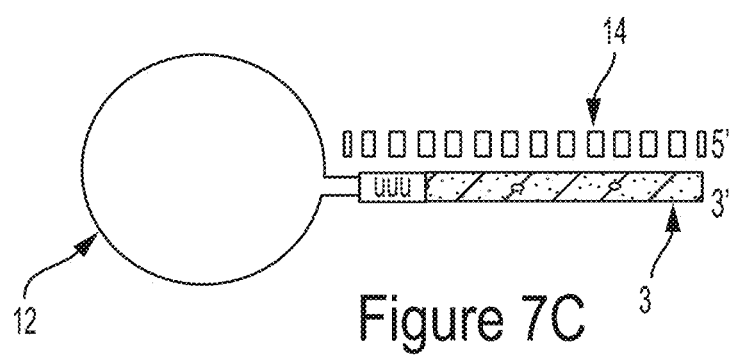
FIG. 7C: A bead composition as illustrated in FIG. 7A further comprising an amplified first read sequence.

In one embodiment, the present invention contemplates a composition comprising a bead (12) attached to an at least one ribonucleotide base linker (i.e., for example, a polyuracil linker sequence), wherein the linker is ligated to at least one read pair sequence where the read pair sequence is derived from a genome (i.e., for example library insert sequence) (3). In one embodiment, the read pair sequence (3) comprises a high throughput sequencing primer adapter sequence. FIG. 7A. In one embodiment, the composition further comprises a first high throughput sequencing primer (13). FIG. 7B. In one embodiment, the composition further comprises an amplified read sequence (14). FIG. 7C.

Figure 8:
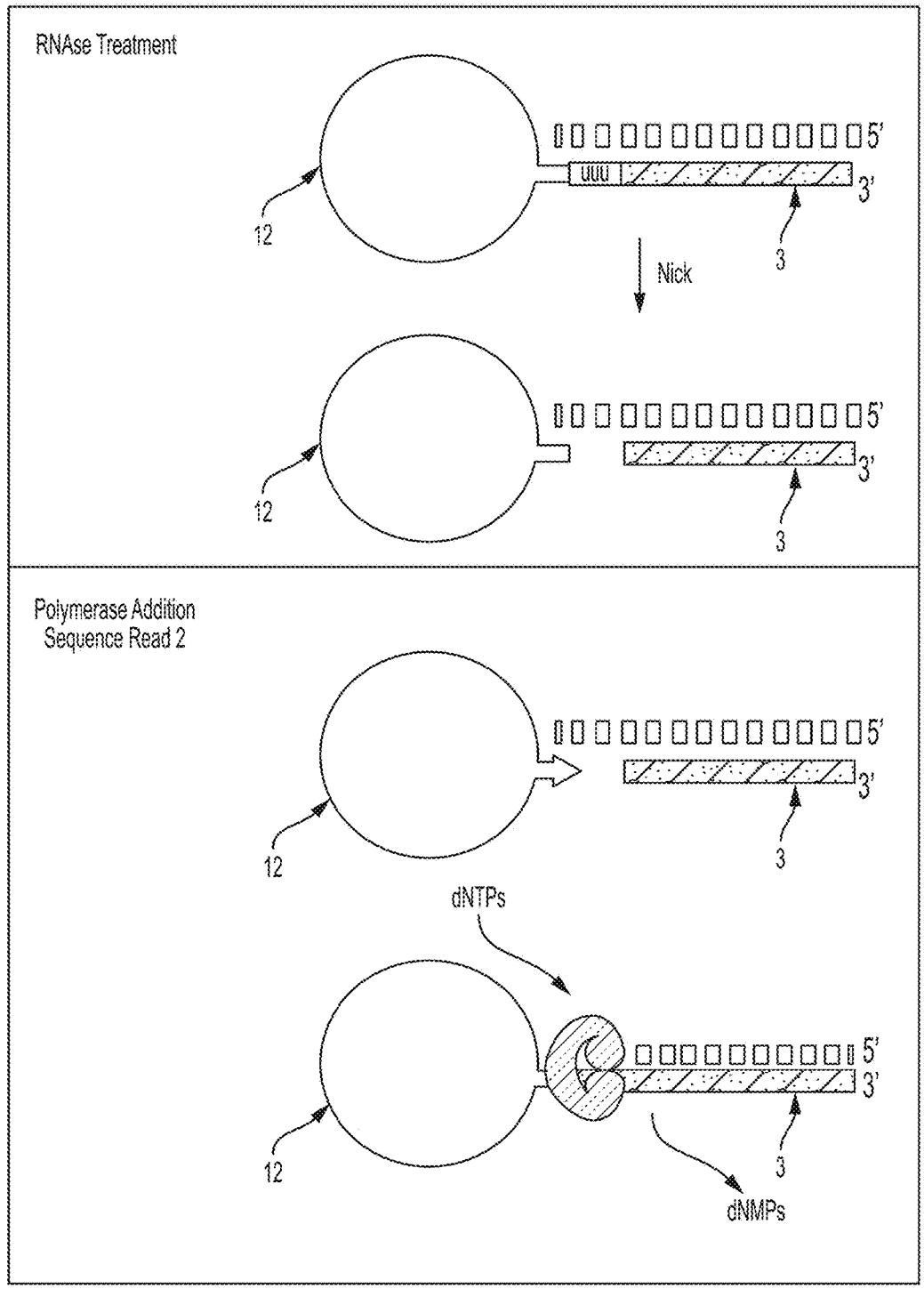
FIG. 8 presents one embodiment of a nick and proofread digestion method to co-amplify a second read pair subsequent to nicking one strand of an amplified first read sequence.

In one embodiment, the present invention contemplates a method comprising: providing; i) a bead (12) attached to an at least one ribonucleotide base linker (i.e., for example, a polyuracil linker), wherein the linker is ligated to at least one read pair sequence where the read pair is derived from a genome (i.e., for example, a library insert sequence) (3); ii) a first high throughput sequencing primer capable of hybridizing to the at least one read pair sequence (3); iii) an ribonuclease enzyme capable of nicking a single strand adjacent to the ribonucleotide base linker; and iv) a polymerase enzyme capable of amplifying a second read sequence; b) hybridizing the first high throughput sequencing primer to the at least one read pair sequence under conditions that amplify a first read sequence (Read 1); c) nicking a single strand adjacent to the ribonucleotide linker with the ribonuclease enzyme, wherein a nick is created; and d) attaching the polymerase to the nick under conditions that amplify a second read sequence (Read 2). FIG. 8.

Similar to the Exonuclease embodiment, Nick & Proofread embodiment creates an oligo with a ribonucleotide base at the 3' end, or within a few bases of the 3' end, attached to a bead. The bead then may goes through the same emulsion amplification process and amplification of Read 1 as described above. After the amplification of Read 1, a ribonuclease enzyme (i.e., for example, an RNase H2 enzyme) may be used to introduce a single-strand nick adjacent to a ribonucleotide base. Although it is not necessary to understand the mechanism of an invention, it is believed that this nick serves as an initiation site for Read 2 when a bst polymerase is used to extend from the nick and displace the existing bottom strand as it progresses.

D. Hairy Beads Method

Figure 9A:
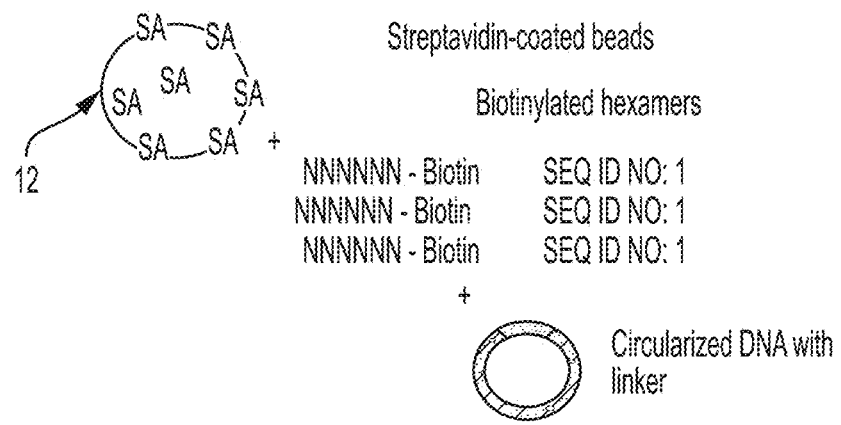
FIG. 9A presents one embodiment of a composition comprising streptavidin (SA) coated beads bound to a plurality of biotin labeled random primer sequences (e.g., NNNNNN-biotin) that are hybridized to a plurality of circularized nucleic acid fragments.

In one embodiment, the present invention contemplates a composition comprising a bead (12) attached to a plurality of streptavidin molecules, wherein the streptavidin molecules are bound to a plurality of biotin labeled random primer sequences. FIG. 9A. For example, the random primer sequence may include but are not limited to hexamers (six nucleotides), heptamers (seven nucleotides), octomers (eight nucleotides) and/or nonomers (nine nucleotides). The random primer sequence therefore comprises an N at each position wherein N may include but is not limited to adenosine (A), thymidine (T), cytosine (C) and/or guanosine (G). Although it is not necessary to understand the mechanism of an invention, it is believed that the random primer sequences comprise roughly an equal mixture of all possible combinations of each base at each position. It is further believed that the random primer sequences can be a mixture of biotinylated and non-biotinylated oligos. The ratio of the mixture of biotinylated to non-biotinylated random primers may range between approximately 10:90 to 90:10, preferably between approximately 20:80 to 80:20, more preferably between approximately 30:70 to 70:30, more preferably between approximately 40:60 to 60:40, but most preferably 50:50. In one embodiment, the random primer sequences are capable of hybridizing to a plurality of nucleic acid fragments (i.e., for example, a library insert sequence). In one embodiment, the random primer is NNNNNN, wherein N is a nucleoside selected from the group consisting of adenosine (A), guanosine (G), thymidine (T) and/or cytosine (C). In one embodiment, the random primer is AGTCCT. In one embodiment, the random primer is TCCTGA. In one embodiment, the random primer is TGATCC.

Figure 9B:
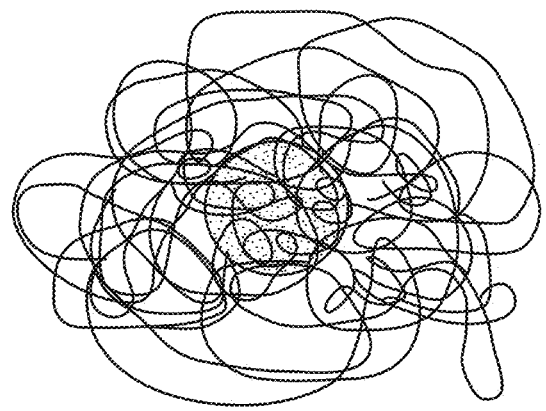
FIG. 9B presents one embodiment of a plurality of co-amplified nucleic acid fragment sequences as shown in FIG. 9A.
Figure 10:
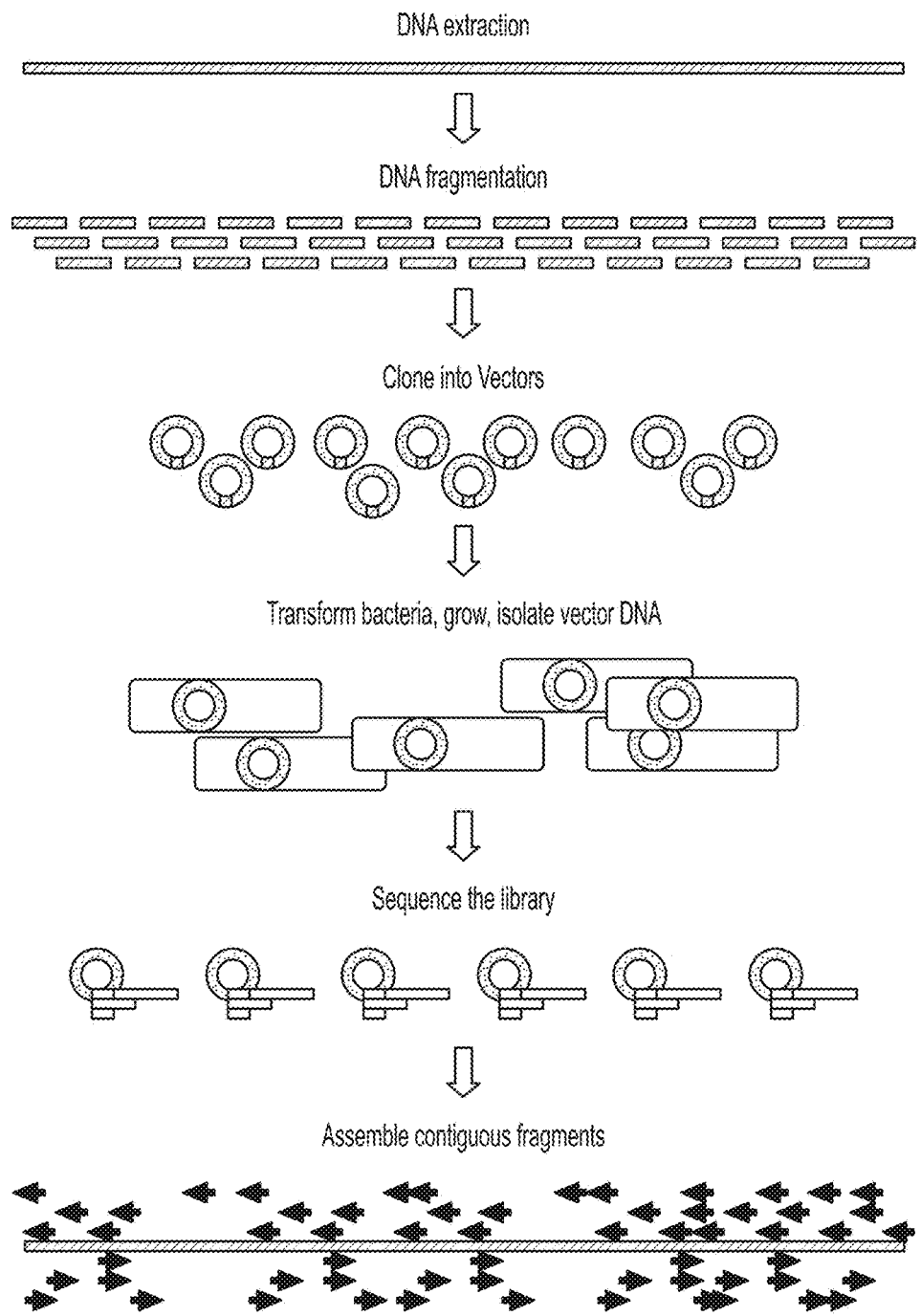
FIG. 10 presents an illustrative schema for the construction of clonal sequencing libraries. Genomic DNA is fragmented into random pieces and cloned as a bacterial library. DNA from individual bacterial clones is sequenced and the sequence is assembled by using overlapping DNA regions.
Figure 11:
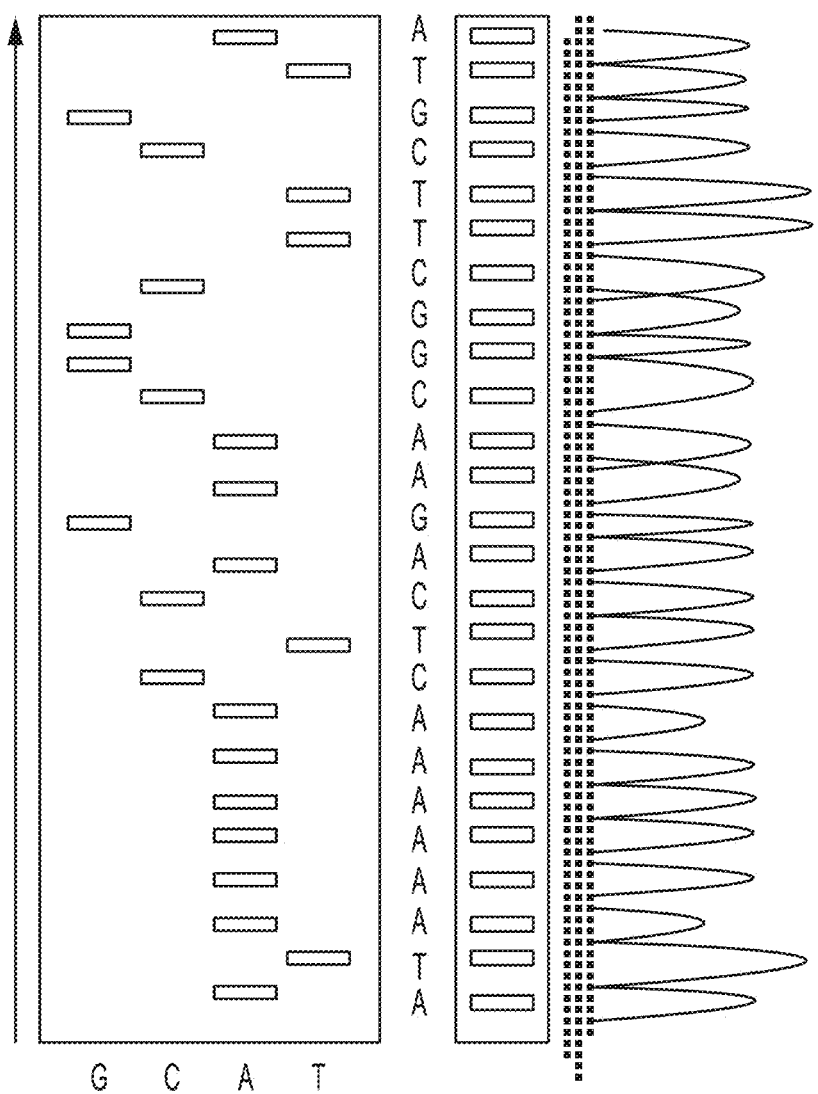
FIG. 11 presents an exemplary illustration of a Sanger chain termination nucleic acid sequence ladder (gel electrophoresis) as compared to their representative fluorescent peaks.

In one embodiment, the plurality of nucleic acid fragments are derived from a single genome. In one embodiment, each of the plurality of nucleic acid fragments is circularized. In one embodiment, each of the plurality of nucleic acid fragments is ligated to a linker nucleic acid sequence. In one embodiment, the linker nucleic acid sequence is double stranded. In one embodiment, the linker nucleic acid sequence comprises at least one high throughput sequencing primer binding site. In one embodiment, the at least one high throughput sequencing primer binding site is a first high throughput sequencing primer binding site. In one embodiment, the at least one high throughput sequencing primer binding site is a second high throughput sequencing primer binding site. In one embodiment, the composition further comprises a plurality of amplified nucleic acid fragments. FIG. 9B.

The amplification of the DNA library using the biotinylated random primers may also be performed before binding to the streptavidin-coated beads. For example, a single piece of circularized (or linear) DNA library may be amplified using phi29 polymerase in the presence of the random primer sequence in solution (i.e., for example, in a test tube, vial, emulsion micro-reactor droplet etc.). The amplified product is then added to the streptavidin-coated beads.

In one embodiment, the present invention contemplates a method, comprising: a) providing; i) a bead coated with a plurality of streptavidin molecules; ii) a plurality of biotin labeled random primer sequences; and iii) a plurality of circularized nucleic acid fragments (i.e., for example, a library insert sequences) derived from a single genome; b) binding the biotin labeled random primer sequences to the streptavidin coated bead; and c) annealing the plurality of circularized nucleic acid fragments to the random primer sequences under conditions that generate an amplified plurality of nucleic acid fragments. In one embodiment, each of the amplified plurality of nucleic acid fragments is attached to the bead. In one embodiment, each of the plurality of nucleic acid fragments comprise a linker nucleic acid sequence. In one embodiment, the linker nucleic acid sequence is double stranded. In one embodiment, the linker nucleic acid sequence comprises at least one high throughput sequencing primer binding site. In one embodiment, the at least one high throughput sequencing primer binding site is a first high throughput sequencing primer binding site. In one embodiment, the at least one high throughput sequencing primer binding site is a second high throughput sequencing primer binding site. In one embodiment, the first high throughput sequencing primer binding site is ligated to a first linker nucleic acid sequence strand. In one embodiment, the second high throughput sequencing primer binding site is ligated to a second linker nucleic acid sequence strand. In one embodiment, the nucleic acid fragment comprises a first read pair sequence and a second read pair sequence. In one embodiment, the method further comprises adding a first high throughput sequencing primer that is complementary to the first high throughput sequencing primer binding site, thereby amplifying the first read pair sequence to generate a first read sequence. In one embodiment, the method further comprises adding a second high throughput sequencing primer that is complementary to the second high throughput sequencing primer binding site, thereby amplifying the second read pair sequence to generate a second read sequence.

In this method, streptavidin coated beads, circularized DNA molecules with a plurality of known linker sequences and biotinylated random primers, or a mixture of biotinylated and non-biotinylated random primers, may be incubated with phi29 polymerase. Although it is not necessary to understand the mechanism of an invention, it is believed that phi29 polymerase will mediate a very processive amplification reaction that uses the random primers to amplify both DNA strands of the nucleic acid fragment simultaneously at multiple sites. Further, if a circular nucleic acid fragment is being amplified, the polymerase is believed to inherently displace the DNA strands such that many copies of the original nucleic acid fragment can be made in a large tangled complex and still remain attached to the bead. Optimally, every amplification primed from a biotinylated random primer can be bound to the beads through the streptavidin-biotin interaction. High throughput sequencing primers (i.e., for example, 454, SOLiD, Illumina and/or ion semiconductor) may be added to the composition as separate oligos that are complementary to portions of the known linker sequence, one pointing in each direction from the end of the linker. These high throughput sequencing primers are added one at a time with Read 1 coming from one primer and Read 2 from the other. The first primer is removed from the composition before the second primer is added (i.e., for example, by melting and/or enzymic degradation). Although it is not necessary to understand the mechanism of an invention, it is believed that the previous amplification of the nucleic acid fragment result in many copies of the read pair sequences such that each Read 1 and Read 2 sequencing primers will bind at many sites along the amplified nucleic acid fragment which is believed to result in a detectable signal.

Although it is not necessary to understand the mechanism of an invention, it is believed that the linker sequences within the circularized amplified nucleic acid fragment products are double-stranded. In some embodiments, a first linker sequence strand comprises a first high throughput sequencing primer binding site that is complementary to a first high throughput sequencing primer. In some embodiment, a second linker sequence strand comprises a second high throughput sequencing primer binding site that is complementary to a second high throughput sequencing primer. Consequently, it is believed that the random-primed phi29 amplification reaction will amplify both strands and so the primers can be annealed to their respective priming sites for sequencing.

III. Conventional Cloning Libraries

In molecular biology, a clone library is generally understood as a collection of DNA fragments that is stored and propagated in a population of microorganisms (i.e., for example, *E. coli*) through the process of molecular cloning. Several different types of DNA libraries have been reported, including, but not limited to, cDNA libraries that are formed from reverse-transcribed RNA and genomic libraries that formed from fragmented genomic DNA. DNA library technology has been developed for many different applications depending upon the source of the original DNA fragments. Further, there are differences in cloning vectors and techniques used in library preparation but, in general, each DNA fragment is uniquely inserted into a cloning vector, wherein a pool of recombinant DNA molecules are then transferred into a population of microorganisms. On average, each microorganism contains one nucleotide construct (i.e., for example, a vector comprising a nucleotide fragment insert). As the population of microorganisms is grown in culture, the DNA inserts are replicated as the microorganisms propagate (i.e., for example, cloned). See, FIG. 7.

A. cDNA Libraries

A cDNA library may represent a sample of the mRNA purified from a particular source (i.e., for example, a collection of cells, a particular tissue, or an entire organism), which has been converted back to a DNA template by reverse transcriptase. Thus, a cDNA library represents genes that were being actively transcribed when the mRNA was purified. Alternatively, cDNA libraries can be generated using techniques that promote "full-length" clones or under conditions that generate shorter fragments used for the identification of "expressed sequence tags". cDNA libraries are useful in reverse genetics, but they only represent a very small (less than 1%) portion of the overall genome in a given organism. Applications of cDNA libraries include, but are not limited to, discovery of novel genes, cloning of full-length cDNA molecules for in vitro study of gene function, mRNA expression profiling, or mRNA alternative splicing patterns.

B. Genomic Libraries

A genomic library may be a set of clones that together represent an entire genome of a given organism (i.e., for example, DNA). The number of individual microbial clones that constitute a genomic library depends on: i) the size of the genome in question; and ii) the DNA insert size tolerated by the particular cloning vector system. For most practical purposes, the tissue source of the genomic DNA is unimportant because each cell of the body contains virtually identical DNA. Useful applications of genomic libraries include, but are not limited to, determining the complete genome sequence of a given organism, serving as a source of genomic sequence for generation of transgenic animals through genetic engineering, identifying regulatory sequence function, and/or identifying genetic mutations responsible for medical conditions.

C. Microbial Transformation

1. Plasmids

A plasmid has been explained to be a DNA molecule that is separate from, and can replicate independently of, the chromosomal DNA. In: Plasmids: Current Research and Future Trends. Lipps G (editor). Caister Academic Press. ISBN 978-1-904455-35-6 (2008). Plasmid DNA may be double stranded and in many cases, spontaneously circularizes. Plasmids usually occur naturally in bacteria, but are sometimes found in eukaryotic organisms (e.g., a 2-micrometer-ring in *Saccharomyces cerevisiae*).

Plasmid size varies from 1 to over 1,000 kilobase pairs (kbp). In: Molecular cloning: a laboratory manual. Russell et al. Cold Spring Harbor, N.Y: Cold Spring Harbor Laboratory (2001); Barnett et al., "Nucleotide sequence and predicted functions of the entire *Sinorhizobium meliloti* pSymA megaplasmid" *PNAS* 98:9883 (2001); Finan et al., "The complete sequence of the 1,683-kb pSymB megaplasmid from the N2-fixing endosymbiont" *PNAS* 98:9889 (2001). The number of identical plasmids within a single cell can range anywhere from one to several thousands.

Plasmids are considered transferable genetic elements, or "replicons", capable of autonomous replication within a suitable host. Similar to viruses, plasmids are not considered a form of "life" as it is currently defined. Simkovics et al., "The Origin and evolution of viruses (a review)" *Acta Microbiol Immunol Hung* 45:349-390 (1998). Unlike viruses, plasmids are considered "naked" DNA and do not encode genes necessary to encase the genetic material for transfer to a new host. Plasmid host-to-host transfer requires direct, mechanical transfer by "conjugation" or changes in host gene expression allowing active uptake of the plasmid by "transformation". Microbial transformation with plasmid DNA also provides a mechanism for horizontal gene transfer within a population of microorganisms.

2. Vectors

Plasmids used in genetic engineering are generally referred to as vectors. Vectors serve as important tools in genetics and biotechnology labs, where they are commonly used to facilitate the expression of integrated genes. Many vectors are commercially available for such uses. For example, a gene desired for replication may be inserted into copies of a vector containing genes that make cells resistant to particular antibiotics, for inserting a multiple cloning site (MCS), and/or a polylinker site. An MCS comprises a short region containing several commonly used restriction sites allowing the easy insertion of DNA fragments at this location. Next, the vectors are inserted into a microorganism (i.e., for example, a bacteria including, but not limited to, *E. coli*) by transformation. Then, the bacteria are exposed to the antibiotic for which the vector imparts a genetic resistance. Consequently, only microorganisms which stably incorporate the vector survive. The microorganisms comprising the vector can be generated into libraries.

However, conventional cloning vectors can usually only contain nucleotide inserts of about 1-10 kb. To clone longer lengths of DNA, lambda phage with lysogeny genes deleted, cosmids, fosmids, bacterial artificial chromosomes or yeast artificial chromosomes could be used.

3. DNA Extraction

In some techniques, the integrated sequences within a vector and/or plasmid are often purified away from the rest of the genome and allows these integrated sequences to be uses to construct other vectors and/or molecular cloning library generation. There are several methods to isolate and purify such plasmid DNA from bacteria, including, but not limited to, the miniprep, the maxiprep, or the bulkprep. The yield is a small amount of impure plasmid DNA. Maxipreps use much larger volumes of bacterial suspension. Essentially, maxipreps are a scaled-up miniprep followed by additional purification. This results in relatively large amounts (i.e., for example, several micrograms) of very pure plasmid DNA. These plasmid preparation methods can be used to obtain large amounts of a plasmid harboring a single cloned insert, or to obtain large amounts of a complex mixture of plasmids collectively harboring an entire library of cloned insert. Commercial kits are currently available that provide reagents and instructions to perform vector and/or plasmid extraction at various scales, purity and levels of automation.

IV. Nucleic Acid Sequencing

The term DNA sequencing refers to sequencing methods for determining the order of the nucleotide bases—adenine, guanine, cytosine, and thymine in a molecule of DNA. Known DNA sequences are presently used for basic biological research, diagnostics, biotechnology, forensic biology, and/or biological systematics. Recent advances in the speed of sequencing (i.e., for example, high throughput sequencing) attained with modern DNA sequencing technology has been instrumental in the sequencing of the human genome, in the Human Genome Project. A comparison has been made of specific characteristics of the most common high throughput sequencing platforms. See, Table I.

TABLE 1

Comparing metrics and performance of next-generation DNA sequencers.

| | Ion Torrent | 454 Sequencing | Illumina | SOLiD |
|---|---|---|---|---|
| Sequencing Chemistry | Ion semiconductor sequencing | Pyrosequencing | Polymerase-based sequence-by-synthesis | Ligation-based sequencing |
| Amplification approach | Emulsion PCR | Emulsion PCR | Bridge amplification | Emulsion PCR |
| Mb per run | 100 Mb | 100 Mb | 600 Gb | 3000 Mb |
| Time per run | 2 hours | 7 hours | 9 days | 5 days |
| Read length | 100 bp | 400 bp | 2 × 100 bp | 35-50 bp |
| Cost per run | $500 USD | $8,438 USD | $20,000 USD | $17,447 USD |
| Cost per Mb | $5.00 USD | $84.39 USD | $0.03 USD | $5.81 USD |
| Cost per instrument | $50,000 USD | $500,000 USD | $600,000 USD | $591,000 USD |

The first DNA sequences were obtained using laborious methods based on two-dimensional chromatography. Following the development of dye-based sequencing methods with automated analysis, DNA sequencing has become easier and faster. Olsvik et al., "Use of automated sequencing of polymerase chain reaction-generated amplicons to identify three types of *cholera* toxin subunit B in *Vibrio cholerae* 01 strains" *J. Clin. Microbiol.* 31:22-25 (1993).

A. Chain Termination Sequencing

The chain-termination method (i.e., for example, the Sanger method) introduced improvements into nucleotide sequencing technology by increasing efficiency, reducing the use of toxic chemicals and/or radioactivity than initial techniques. Chain termination sequencing introduced the use of dideoxynucleotide triphosphates (ddNTPs) as DNA chain terminators.

A classical chain-termination method usually comprises a single-stranded DNA template, a DNA primer, a DNA polymerase, radioactively or fluorescently labeled nucleotides, and modified nucleotides that terminate DNA strand elongation. The DNA sample is divided into four separate sequencing reactions, containing all four of the standard deoxynucleotides (e.g., dATP, dGTP, dCTP and dTTP) and the DNA polymerase. To each reaction is added only one of the four dideoxynucleotides (e.g., ddATP, ddGTP, ddCTP, or ddTTP) which are the chain-terminating nucleotides. These dideoxynucleotides lack a 3'-OH group required for the formation of a phosphodiester bond between two nucleotides, thus terminating DNA strand extension and resulting in DNA fragments of varying length.

Newly synthesized and labeled DNA fragments are heat denatured, and separated by size (i.e., for example, with a resolution of just one nucleotide) by gel electrophoresis on a denaturing polyacrylamide-urea gel with each of the four reactions run in one of four individual lanes (lanes A, T, G, C); the DNA bands are then visualized by autoradiography or UV light, and the DNA sequence can be directly read off the X-ray film or gel image, wherein dark bands on the gel correspond to DNA fragments of different lengths. For example, a dark band in a lane indicates a DNA fragment that is the result of chain termination after incorporation of a dideoxynucleotide (ddATP, ddGTP, ddCTP, or ddTTP). The relative positions of the different bands among the four lanes are then used to read (from bottom to top) the DNA sequence. See, FIG. 8.

B. Next-Generation Sequencing

Next-generation sequencing technologies (i.e., for example, high throughput sequencing) parallelize the sequencing process and results in a low-cost method that simultaneously produces thousands or millions of sequences. Hall N., "Advanced sequencing technologies and their wider impact in microbiology" *J. Exp. Biol.* 210 (Pt 9): 1518-1525 (2007); and Church. G., "Genomes for all" *Sci. Am.* 294: 46-54 (2006). Advantages of next-generation sequence reads including but not limited to: i) the length of a sequence read from most current next-generation platforms is shorter than that from a capillary sequencer; and ii) each next-generation read type has a unique error model different from that already established for capillary sequence reads. Both differences affect how the reads are utilized in bioinformatic analyses, depending upon the application. For example, in strain-to-reference comparisons (i.e., for example, re-sequencing), the typical definition of repeat content must be revised in the context of the shorter read length. In addition, a much higher read coverage or sampling depth is required for comprehensive resequencing with short reads to adequately cover the reference sequence at the depth and low gap size needed. Some applications are more suitable for certain platforms than others, as detailed below. Furthermore, read length and error profile issues entail platform- and application-specific bioinformatics-based considerations. Moreover, it is important to recognize the significant impacts that implementation of these platforms in a production sequencing environment has on informatics and bioinformatics infrastructures.

Several techniques for massively parallel DNA sequencing have recently been described. Ronaghi et al., "Analyses of secondary structures in DNA by pyrosequencing" *Anal Biochem* 267: 65-71 (1999); Brenner et al., "Gene expression analysis by massively parallel signature sequencing (MPSS) on microbead arrays" *Nat Biotechnol* 18:630-634 (2000); Braslaysky et al., Sequence information can be obtained from single DNA molecules" *Proc Natl Acad Sci* 100:3960-3964 (2003); Margulies et al., "Genome sequencing in microfabricated high-density picoliter reactors" *Nature* 437:376-380 (2005); Shendure et al., "Accurate multiplex polony sequencing of an evolved bacterial genome" *Science* 309:1728-1732 (2005); Ju et al., "Four-color DNA sequencing by synthesis using cleavable fluorescent nucleotide reversible terminators" *Proc Natl Acad Sci* 103:19635-19640 (2006); Gibbs et al., "Evolutionary and biomedical insights from the rhesus macaque genome" *Science* 316:222-234 (2007); Bentley et al., "Accurate whole human genome sequencing using reversible terminator chemistry" *Nature* 456:53-59 (2008); and Eid et al., "Real-time DNA sequencing from single polymerase molecules" *Science* 323:133-138 (2009).

These techniques broadly fall into at least two assay categories (i.e., for example, polymerase and/or ligase based) and/or at least two detection categories (i.e., for example, asynchronous single molecule and/or synchronous multi-molecule readouts). For example, SOLiD (Sequencing by Oligo Ligation Detection) sequencing comprises a DNA ligase-based synchronous ensemble detection method utilized to read 500 million to over 1 billion reads per instrument run. Cloonan et al., "Stem cell transcriptome profiling via massive-scale mRNA sequencing" *Nat Methods* 5:613-619 (2008); and Valouev et al., "A high-resolution, nucleosome position map of *C. elegans* reveals a lack of universal sequence-dictated positioning" *Genome Res* 18:1051-1063 (2008).

All of these techniques are theoretically compatible with mate-paired sequencing, but they differ in how they generate the mate-paired reads. For example, one approach generates short pairs from cluster polymerase chain reaction (PCR) colonies often referred to as "paired-ends." Campbell et al., "Identification of somatically acquired rearrangements in cancer using genome-wide massively parallel paired-end sequencing" *Nat Genet* 40: 722-729 (2008). These paired-end reads have limited insert sizes due to the efficiency and representation of PCR amplification of long amplicons via cluster PCR. Consequently, very few paired-end reads are generated that are longer than a Sanger capillary electrophoresis read (<$10^3$ clone coverage in pairs >1.0 kb).

DNA circularization and random shearing have been used, thereby circumventing the need to PCR amplify the entire pairing distance at the cost of more input DNA. Korbel et al., "Paired-end mapping reveals extensive structural variation in the human genome" *Science* 318: 420-426 (2007); and Bentley et al., "Accurate whole human genome sequencing using reversible terminator chemistry" *Nature* 456:53-59 (2008). These pairs each differ substantially in their tag length due to the random shearing step. The asymmetrical tag lengths reduce the pairing efficiency and often contaminate the library prep with a high number of 200-bp inserts; thus, no more than 100× clone coverage is obtained, and many tags are sequenced that are not paired or are paired in the wrong distance or orientation. Furthermore, these techniques may result in many inverted molecules that complicate the detection of inversions.

A preferred pairing method would provide both high sequence coverage and high clone or "physical" coverage with flexible insert sizes such that SNPs, small indels, larger structural variations, and copy number variants (CNVs) could be surveyed in one method. Two pairing methods can be used that retain less variable tag lengths while enabling both high sequence coverage and high clone coverage of the human genome to enable the broadest survey of variation possible. Use of ligases for massively parallel short-read DNA sequencing of human genomes offers several unique attributes next to polymerases. Most notable is the use of an error-correcting probe-labeling scheme (two-base encoding, or 2BE), which provides error correction concurrent with the color-called alignment of the data (i.e., for example, without having to resequence the reads). This correction property has specific utility in bisulfite sequencing, de novo assembly, indel detection, and SNP detection.

SOLiD sequencing is believed capable of efficiently surveying single nucleotide polymorphisms and many forms of structural variation concurrently at relatively modest coverage levels. Such an expansive clone coverage allows identification of a larger number of structural variants in a size range not efficiently explored in previous studies.

The massively parallel scale of sequencing implies a similarly massive scale of computational analyses that include image analysis, signal processing, background subtraction, base calling, and quality assessment to produce the final sequence reads for each run. In every case, these analyses place significant demands on the information technology (IT), computational, data storage, and laboratory information management system (LIMS) infrastructures extant in a sequencing center, thereby adding to the overhead required for high-throughput data production. This aspect of next-generation sequencing is at present complicated by the dearth of current sequence analysis tools suited to shorter sequence read data; existing data analysis pipelines and algorithms must be modified to accommodate these shorter reads. In many cases, and certainly for new applications of next-generation sequencing, entirely new algorithms and data visualization interfaces are being devised and tested to meet this new demand. Therefore, the next-generation platforms are effecting a complete paradigm shift, not only in the organization of large-scale data production, but also in the downstream bioinformatics, IT, and LIMS support required for high data utility and correct interpretation.

This paradigm shift promises to radically alter the path of biological inquiry, as the following review of recent endeavors to implement next-generation sequencing platforms and accompanying bioinformatics-based analyses serves to substantiate.

Most massively parallel high throughput sequencing techniques avoid molecular cloning in a microbial host (i.e., for example, transformed bacteria, such as *E. coli*) to propagate the DNA inserts. Instead, they use in vitro clonal PCR amplification strategies to meet the molecular detection sensitivities of the current molecule sequencing technologies. Some sequencing platforms (e.g., Helicos Biosciences) avoid amplification altogether and sequence single, unamplified DNA molecules. With or without clonal amplification, the available yield of unique sequencing templates has a significant impact on the total efficiency of the sequencing process. Various clonal amplification methods have been described in more detail below 1. Emulsion Amplification Emulsion PCR is generally used to isolate individual DNA molecules along with primer-coated beads in aqueous droplets within an oil phase. An ensuing polymerase chain reaction process then coats each bead with clonal copies of the DNA molecule followed by immobilization for later sequencing. Emulsion PCR is more commonly referred to as: i) 454 sequencing (Margulies et al., "Genome sequencing in microfabricated high-density picoliter reactors" *Nature* 437:376-380 (2005); ii) polony sequencing (Shendure, J. "Accurate Multiplex Polony Sequencing of an Evolved Bacterial Genome" *Science* 309:1728 (2005); and iii) SOLiD sequencing (Applied Biosystems).

454 sequencing techniques employ pyrosequencing that uses DNA polymerization by adding one nucleotide species at a time and detecting and quantifying the number of nucleotides added to a given location through the light emitted by the release of attached pyrophosphates. Ronaghi et al., "Real-time DNA sequencing using detection of pyrophosphate release" *Analytical Biochemistry* 242: 84-89 (1996).

The SOLiD platform uses an adapter-ligated fragment library similar to those of the other next-generation platforms, and uses an emulsion PCR approach with small magnetic beads to amplify the fragments for sequencing. Unlike the other platforms, SOLiD uses DNA ligase and a unique approach to sequence the amplified fragments. Two flow cells are processed per instrument run, each of which can be divided to contain different libraries in up to four quadrants. Read lengths for SOLiD are user defined between 25-50 bp, and each sequencing run yields up to ~100 Gb of DNA sequence data. Once the reads are base called, have quality values, and low-quality sequences have been removed, the reads are aligned to a reference genome to enable a second tier of quality evaluation called two-base encoding. The principle of two-base encoding illustrates how this approach works to differentiate true single base variants from base-calling errors.

2. Bridge Amplification

Bridge PCR also involves in vitro clonal amplification, wherein the cloned fragments are amplified using primers that are attached to a solid surface. Such configurations are compatible with an Illumina Genome Analyzer. For example, DNA molecules are physically bound to a surface such that they may be sequenced in parallel (i.e., for example, known in the art as massively parallel sequencing).

Sequencing by synthesis techniques (i.e., for example, dye-termination electrophoretic sequencing) uses a DNA polymerase to determine the base sequence. Alternatively, a reversible terminator method may be used wherein fluorescently labeled nucleotides are individually added, such that each position is determined in real time (i.e., for example, Illumina). A blocking group on each labeled nucleotide is then removed to allow polymerization of another nucleotide.

Massively parallel sequencing of millions of fragments has been successfully commercialized by a reversible terminator-based sequencing chemistry (Illumina) This sequencing technology offers a highly robust, accurate, and scalable system that is cost-effective, and sufficiently accurate to support next-generation sequencing technologies. For example, the Illumina sequencing technology relies on the attachment of randomly fragmented genomic DNA to a planar, optically transparent surface. These attached DNA fragments are extended and bridge amplified to create an ultra-high density sequencing flow cell with hundreds of millions of clusters, each containing ~1,000 copies of the same template. These templates are sequenced using a robust four-color DNA sequencing-by-synthesis technology that employs reversible terminators with removable fluorescent dyes. This approach ensures high accuracy and true base-by-base sequencing, eliminating sequence-context specific errors and enabling sequencing through homopolymers and repetitive sequences.

High-sensitivity fluorescence detection may be achieved using laser excitation and total internal reflection optics. Sequence reads are aligned against a reference genome and genetic differences are called using specially developed data analysis pipeline software. Alternative sample preparation methods allow the same system to be used for a range of applications including gene expression, small RNA discovery, and protein-nucleic acid interactions.

After completion of the first read, the templates can be regenerated in situ to enable a second 75+ bp read from the opposite end of the fragments. A paired-end module directs the regeneration and amplification operations to prepare the templates for the second round of sequencing. First, the newly sequenced strands are stripped off and the complementary strands are bridge amplified to form clusters. Once the original templates are cleaved and removed, the reverse strands undergo sequencing-by-synthesis. The second round of sequencing occurs at the opposite end of the templates, generating 75+ bp reads for a total of >20 Gb of paired-end data per run.

A single molecule amplification step compatible with the Illumina Genome Analyzer may start with an Illumina-specific adapter library and takes place on an oligo-derivatized surface of a flow cell. A flow cell comprises an 8-channel sealed glass microfabricated device that allows bridge amplification of fragments on its surface, and uses DNA polymerase to produce multiple DNA copies (i.e., for example, DNA clusters) wherein each cluster represents a single molecule that initiated the cluster amplification. A separate library can be added to each of the eight channels, or the same library can be used in all eight, or combinations thereof. Each cluster may contain approximately one million amplicons (e.g., copies) of the original fragment, which is sufficient for reporting incorporated bases at the required signal intensity for detection during sequencing.

The Illumina system utilizes a sequencing-by-synthesis approach in which all four nucleotides are added simultaneously to the flow cell channels, along with DNA polymerase, for incorporation into the oligo-primed cluster fragments. Specifically, the nucleotides carry a base-unique fluorescent label and the 3'-OH group is chemically blocked such that each incorporation is a unique event. An imaging step follows each base incorporation step, during which each flow cell lane is imaged in three 100-tile segments by the instrument optics at a cluster density per tile of 300,000 or more. After each imaging step, the 3' blocking group is chemically removed to prepare each strand for the next incorporation by DNA polymerase. This series of steps continues for a specific number of cycles, as determined by user-defined instrument settings, which permits discrete read lengths of 75+ bases. A base-calling algorithm assigns sequences and associated quality values to each read and a quality checking pipeline evaluates the Illumina data from each run, removing poor-quality sequences.

For example, a high-density single-molecule arrays of genomic DNA fragments may be attached to the surface of the flow cell reaction chamber and used isothermal 'bridging' amplification to form DNA 'clusters' from each fragment. In such an array, the DNA in each cluster single stranded and added a universal primer for sequencing. For paired read sequencing, the DNA templates are converted to double-stranded DNA and removed the original strands, leaving the complementary strand as template for the second sequencing reaction. To obtain paired reads separated by larger distances, DNA fragments may be circularized of the required length short junction fragments are constructed to support paired end sequencing. Bentley et al., "Accurate whole human genome sequencing using reversible terminator chemistry" *Nature* 456:53-59 (2008).

C. Shotgun Sequencing

In genetics, shotgun sequencing, also known as shotgun cloning, is generally referred to as a method used for sequencing long DNA strands. It is named by analogy with the rapidly-expanding, quasi-random firing pattern of a shotgun. Since the chain termination method of DNA sequencing can only be used for fairly short strands (i.e., for example, 100 to 1000 basepairs), longer sequences must be subdivided into smaller fragments, and subsequently reassembled to give the overall sequence. Two principal methods are used for this: chromosome walking, which progresses through the entire strand, piece by piece, and shotgun sequencing, which is a faster but more complex process, and uses random fragments.

In shotgun sequencing, DNA is broken up randomly into numerous small segments, which have been conventionally sequenced using the chain termination method to obtain reads. Multiple overlapping reads for the target DNA are obtained by performing several rounds of this fragmentation and sequencing. Computer programs then use the overlapping ends of different reads to assemble them into a continuous sequence. Staden R., "A strategy of DNA sequencing employing computer programs" *Nucleic Acids Research* 6: 2601-2610 (1979) and Anderson S., "Shotgun DNA sequencing using cloned DNase I-generated fragments" *Nucleic Acids Research* 9:3015-3027 (1981). For example, a single nucleic acid sequence may be sequenced as two separate fragments, wherein each fragment comprises two reads, the respective 3'-5' strand and the 5'-3' strand. None of the four different reads cover the full length of the original sequence. However, the four reads can be assembled into the original sequence using nucleic acid sequence overlap of their ends, that both to align and order the respective reads. The original shotgun sequencing method had disadvantages by necessitating the processing an enormous amount of information that generated ambiguities and sequencing errors. Assembly of complex genomes is additionally complicated by the great abundance of repetitive sequence, meaning similar short reads could come from completely different parts of the sequence.

Consequently, numerous overlapping read segments for each fragment of original DNA are necessary to overcome these difficulties and accurately assemble the sequence. For example, to complete the Human Genome Project, most of the human genome was sequenced at 12× or greater coverage; that is, each base in the final sequence was present, on average, in 12 reads.

Whole genome shotgun sequencing for small (i.e., for example, 4,000 to 7,000 base pairs) genomes gave way to a broader application that benefited from pair-wise end sequencing. Pair wise end sequencing performs sequencing from both ends of a read simultaneously, instead of a linear left-right process. Although sequencing both ends of the same fragment and keeping track of the paired data was more cumbersome than sequencing a single end of two distinct fragments, the knowledge that the two sequences were oriented in opposite directions and were about the length of a fragment apart from each other was valuable in reconstructing the sequence of the original target fragment.

Paired end sequencing was first reported as part of the sequencing of the human HGPRT locus, although the use of paired ends was limited to closing gaps after the application of a traditional shotgun sequencing approach. Edwards et al., "Closure strategies for random DNA sequencing". *Methods: A Companion to Methods in Enzymology* 3: 41-47 (1991). A theoretical description of a pure pair-wise end sequencing strategy assuming fragments of constant length was also reported. Edwards et al., "Automated DNA sequencing of the human HPRT locus" *Genomics* 6:593-608 (1990). The method was improved by demonstrating that pair wise sequencing could be performed using fragments of varying sizes, thereby demonstrating a pair-wise end-sequencing strategy would be possible on large genomic targets. Roach et al., "Pair-wise end sequencing: a unified approach to genomic mapping and sequencing" *Genomics* 26:345-353 (1995). This strategy was successfully employed to sequence the genomes of *Haemophilus influenzae, Drosophila melanogaster*, and *Homo sapiens*. Fleischmann et al., "Whole-genome random sequencing and assembly of *Haemophilus influenzae* Rd.". Science 269 (5223):496-512 (1995); and Adams et al., "The genome sequence of *Drosophila melanogaster*". Science 287 (5461): 2185-2195 (2000).

To apply pair wise sequencing to high-molecular-weight DNA, the DNA can be sheared into random fragments, size-selected (i.e., for example, 2, 10, 50, and/or 150 kb), and cloned into an appropriate vector. The clones are then sequenced from both ends using the chain termination method yielding two short sequences. Each sequence is called an end-read, or read, wherein two reads from the same clone are referred to as mate pairs. Since the chain termination method usually can only produce reads between 500 and 1000 bases long, in all but the smallest clones, mate pairs will rarely overlap. The original DNA sequence is reconstructed from the numerous reads using sequence assembly software. First, overlapping reads are collected into longer composite sequences known as contigs. Contigs can be linked together into scaffolds by following connections between mate pairs. The distance between contigs can be inferred from the mate pair positions if the average fragment length of the library is known and has a narrow window of deviation. Conventional pair wise sequencing has disadvantages including but not limited to a need to improve reliability to correctly link regions, particularly for genomes with repeating regions.

Although shotgun sequencing was the most advanced technique for sequencing genomes from about 1995-2005, other technologies surfaced, called next-generation sequencing (supra). These technologies produce shorter reads (anywhere from 25-500 bps) but many hundreds of thousands or millions of reads are processed in a relatively short time (i.e., for example, within twenty-four hours). This results in high coverage, but the assembly process is much more computationally expensive. These technologies are vastly superior to chain termination shotgun sequencing due to the high volume of data and the relatively short time it takes to sequence a whole genome.

D. Ion Semiconductor Sequencing

Ion Semiconductor Sequencing is a method of DNA sequencing based on the detection of hydrogen ions that are released during DNA amplification. This is a method of "sequencing by synthesis", during which a complementary strand is built based on the sequence of a template stand.

For example, a microwell containing a template DNA strand to be sequenced can be flooded with a single species of deoxyribonucleotide (dNTP). If the introduced dNTP is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple dNTP molecules will be incorporated in a single cycle. This leads to a corresponding number of released hydrogens and a proportionally higher electronic signal.

This technology differs from other sequencing technologies (supra) in that no modified nucleotides or optics are used. Ion semiconductor sequencing may also be referred to as ion torrent sequencing, pH-mediated sequencing, silicon sequencing, or semiconductor sequencing. Ion semiconductor sequences was developed by Ion Torrent Systems Inc. and may be performed using a bench top machine. Rusk, N. (2011). "Torrents of sequence". Nat Meth 8(1): 44-44.

Although it is not necessary to understand the mechanism of an invention, it is believed that hydrogen ion release occurs during nucleic acid amplification because of the formation of a covalent bond and the release of pyrophosphate and a positively charged hydrogen ion. Ion semiconductor sequencing exploits these facts by determining if a hydrogen ion is released upon providing a single species of dNTP to the reaction.

For example, microwells on a semiconductor chip that each contain one single-stranded template DNA molecule to be sequenced and one DNA polymerase can be sequentially flooded with unmodified A, C, G or T dNTP. Pennisi, E. (2010). "Semiconductors inspire new sequencing technologies" *Science* 327(5970): 1190; and Perkel, J., "Making contact with sequencing's fourth generation" *Biotechniques* (2011). The hydrogen ion that is released in the reaction changes the pH of the solution, which is detected by a hypersensitive ion sensor. The unattached dNTP molecules are washed out before the next cycle when a different dNTP species is introduced.

Beneath the layer of microwells is an ion sensitive layer, below which is a hypersensitive ISFET ion sensor. All layers are contained within a CMOS semiconductor chip, similar to that used in the electronics industry. Each released hydrogen ion triggers the ISFET ion sensor. The series of electrical pulses transmitted from the chip to a computer is translated into a DNA sequence, with no intermediate signal conversion required. Each chip contains an array of microwells with corresponding ISFET detectors. Because nucleotide incorporation events are measured directly by electronics, the use of labeled nucleotides and optical measurements are avoided.

VI. Polymerase Chain Reaction

A. Conventional Polymerase Chain Reaction

The polymerase chain reaction (PCR) is a technique in molecular biology to amplify a single or few copies of a piece of DNA across several orders of magnitude, generating thousands to millions of copies of a particular DNA sequence. The method relies on thermal cycling, consisting of cycles of repeated heating and cooling of the reaction for DNA melting and enzymatic replication of the DNA. Primers (short DNA fragments) containing sequences complementary to the target region along with a DNA polymerase (after which the method is named) are key components to enable selective and repeated amplification. As PCR progresses, the DNA generated is itself used as a template for replication, setting in motion a chain reaction in which the DNA template is exponentially amplified. PCR can be extensively modified to perform a wide array of genetic manipulations.

Almost all PCR applications employ a heat-stable DNA polymerase, such as Taq polymerase, an enzyme originally isolated from the bacterium *Thermus aquaticus*. This DNA polymerase enzymatically assembles a new DNA strand from DNA building blocks, the nucleotides, by using single-stranded DNA as a template and DNA oligonucleotides (also called DNA primers), which are required for initiation of DNA synthesis. The vast majority of PCR methods use thermal cycling, i.e., alternately heating and cooling the PCR sample to a defined series of temperature steps. These thermal cycling steps are necessary first to physically separate the two strands in a DNA double helix at a high temperature in a process called DNA melting. At a lower temperature, each strand is then used as the template in DNA synthesis by the DNA polymerase to selectively amplify the target DNA. The selectivity of PCR results from the use of primers that are complementary to the DNA region targeted for amplification under specific thermal cycling conditions. In one embodiment, the present invention contemplates a method comprising, amplifying a plurality of a complex mixture ("library") of DNA molecules by PCR, wherein each DNA molecule carries the same pair of universal terminal sequence attachments.

PCR is used to amplify a specific region of a DNA strand (the DNA target). Most PCR methods typically amplify DNA fragments of up to ~10 kilo base pairs (kb), although some techniques allow for amplification of fragments up to 40 kb in size. Cheng et al., "Effective amplification of long targets from cloned inserts and human genomic DNA" *Proc Natl Acad Sci*. 91: 5695-5699 (1994). A basic PCR set up usually involves several components and reagents. "Chapter 8: In vitro Amplification of DNA by the Polymerase Chain Reaction" In: Molecular Cloning: A Laboratory Manual (3rd ed.) Sambrook et al. (Eds). Cold Spring Harbor, N.Y.: Cold Spring Harbor Laboratory Press. ISBN 0-87969-576-5 (2001). These components may include, but are not limited to: i) DNA template that contains the DNA region (target) to be amplified; ii) two primers that are complementary to the 3' ends of each of the sense and anti-sense strand of the DNA target; iii) Taq polymerase or another DNA polymerase with a temperature optimum at around 70° C.; iv) deoxynucleoside triphosphates (dNTPs; also very commonly and erroneously called deoxynucleotide triphosphates), the building blocks from which the DNA polymerases synthesizes a new DNA strand; v) buffer solution, providing a suitable chemical environment for optimum activity and stability of the DNA polymerase; vi) divalent cations, magnesium or manganese ions; generally $Mg^{2+}$ is used, but $Mn^{2+}$ can be utilized for PCR-mediated DNA mutagenesis, as higher $Mn^{2+}$ concentration increases the error rate during DNA synthesis (Pavlov et al., "Recent developments in the optimization of thermostable DNA polymerases for efficient applications" *Trends Biotechnol*. 22: 253-260 (2004)); and vii) monovalent cation potassium ions.

The PCR is commonly carried out in a reaction volume of 10-200 μl in small reaction tubes (0.2-0.5 ml volumes) in a thermal cycler. The thermal cycler heats and cools the reaction tubes to achieve the temperatures required at each step of the reaction. Many modern thermal cyclers make use of the Peltier effect which permits both heating and cooling of the block holding the PCR tubes simply by reversing the electric current. Thin-walled reaction tubes permit favorable thermal conductivity to allow for rapid thermal equilibration. Most thermal cyclers have heated lids to prevent condensation at the top of the reaction tube, but a layer of oil or a ball of wax may also be effective.

VIII. Barcodes

DNA barcoding is a taxonomic method that uses a short genetic marker in an organism's DNA to identify it as belonging to a particular species. It differs from molecular phylogeny in that the main goal is not to determine classification but to identify an unknown sample in terms of a known classification. Kress et al., "Use of DNA barcodes to identify flowering plants" *Proc. Natl. Acad. Sci. U.S.A.* 102(23):8369-8374 (2005). Barcodes are sometimes used in an effort to identify unknown species or assess whether species should be combined or separated. Koch H., "Combining morphology and DNA barcoding resolves the taxonomy of Western Malagasy Liotrigona Moure, 1961" *African Invertebrates* 51(2): 413-421 (2010); and Seberg et al., "How many loci does it take to DNA barcode a crocus?" *PLoS One* 4(2):e4598 (2009). Barcoding has been used, for example, for identifying plant leaves even when flowers or fruit are not available, identifying the diet of an animal based on stomach contents or feces, and/or identifying products in commerce (for example, herbal supplements or wood). Soininen et al., "Analysing diet of small herbivores: the efficiency of DNA barcoding coupled with high-throughput pyrosequencing for deciphering the composition of complex plant mixtures" *Frontiers in Zoology* 6:16 (2009).

It has been suggested that a desirable locus for DNA barcoding should be standardized so that large databases of sequences for that locus can be developed. Most of the taxa of interest have loci that are sequencable without species-specific PCR primers. CBOL Plant Working Group, "A DNA barcode for land plants" *PNAS* 106(31):12794-12797 (2009). Further, these putative barcode loci are believed short enough to be easily sequenced with current technology. Kress et al., "DNA barcodes: Genes, genomics, and bioinformatics" *PNAS* 105(8):2761-2762 (2008). Consequently, these loci would provide a large variation between species in combination with a relatively small amount of variation within a species. Lahaye et al., "DNA barcoding the floras of biodiversity hotspots" *Proc Natl Acad Sci USA* 105(8): 2923-2928 (2008).

DNA barcoding is based on a relatively simple concept. For example, most eukaryote cells contain mitochondria, and mitochondrial DNA (mtDNA) has a relatively fast mutation rate, which results in significant variation in mtDNA sequences between species and, in principle, a comparatively small variance within species. A 648-bp region of the mitochondrial cytochrome c oxidase subunit I (COI) gene was proposed as a potential 'barcode'. As of 2009, databases of CO1 sequences included at least 620,000 specimens from over 58,000 species of animals, larger than databases available for any other gene. Ausubel, J., "A botanical macroscope" *Proceedings of the National Academy of Sciences* 106(31):12569 (2009).

Software for DNA barcoding requires integration of a field information management system (FIMS), laboratory information management system (LIMS), sequence analysis tools, workflow tracking to connect field data and laboratory data, database submission tools and pipeline automation for scaling up to eco-system scale projects. Geneious Pro can be used for the sequence analysis components, and the two plugins made freely available through the Moorea Biocode Project, the Biocode LIMS and Genbank Submission plugins handle integration with the FIMS, the LIMS, workflow tracking and database submission.

IX. Kits

In one embodiment, the present invention contemplates a kit comprising: a) a first container comprising a solid substrate capable of attaching a first read pair and a second read pair, wherein said first and second read pairs are derived from a library nucleic acid insert sequence; b) a second container comprising a first high throughput sequencing primer capable of amplifying said first read pair and a second high throughput sequencing primer capable of amplifying said second read pair and c) instructions for amplifying simultaneously said first and second read pairs with said first and second primers. In one embodiment, the solid substrate comprises a bead. In one embodiment, the solid substrate comprises a microwell. In one embodiment, the instructions provide attaching the first and said second read pair sequences to said solid substrate as separate sequences. In one embodiment, the instructions provide attaching the first and said second read pair sequences to said solid substrates as a single sequence. In one embodiment, the first read pair sequence comprises a first high throughput sequencing primer binding site. In one embodiment, the second read pair sequence comprises a second high throughput sequencing primer binding site. In one embodiment, the instructions provide amplifying the first read pair sequence with the first high throughput sequencing primer. In one embodiment, the instructions provide removing the first high throughput sequencing primer from the first amplified read pair. In one embodiment, the instructions provide amplifying the second read pair sequence with the second high throughput sequencing primer. In one embodiment, the instructions provide removing the second high throughput sequencing primer from the second read pair. In one embodiment, the kit further comprises a third container comprising at least one enzyme. In one embodiment, the enzyme may including but not limited to an exonuclease enzyme (e.g., exonuclease III) or a ribonuclease enzyme. In one embodiment, the first and second high throughput sequencing primers are 454 sequencing primers. In one embodiment, the first and second high throughput sequencing primers are Illumina sequencing primers. In one embodiment, the first and second high throughput sequencing primers are SOLiD sequencing primers. In one embodiment, the first and second high throughput sequencing primers are ion semiconductor sequencing primers. In one embodiment, the instructions provide performing the simultaneous amplification in a single reaction mixture.

For example, the kit can optionally include enzymes such as DNA polymerase, Taq polymerase, PCR primers and/or restriction enzymes. The kits may also optionally include appropriate systems (e.g. opaque containers) or stabilizers (e.g. antioxidants) to prevent degradation of the reagents by light or other adverse conditions.

The kits may optionally include instructional materials containing directions (i.e., protocols) providing for the use of the compositions and/or reagents in the present invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

We claim:

1. A method, comprising:
 a) providing:
  i) a solid substrate that can be attached to at least one nucleic acid sequence bearing an attachment feature;
  ii) a plurality of random primers comprising random primers bearing an attachment feature and lacking a universal sequence and random primers that do not bear said attachment feature, wherein the ratio of random primers bearing the attachment feature to random primers not bearing the attachment feature is between 30:70 and 70:30; and
  iii) a plurality of nucleic acid fragments, comprising a plurality of subsequences and lacking terminal universal sequences;
 b) annealing said plurality of nucleic acid fragments to said plurality of random primers under conditions that generate a plurality of linear amplified nucleic acid fragments incorporating said attachment feature; and
 c) combining the solid substrate under conditions that attach the solid substrate, through the attachment feature, with either
  (1) the plurality of random primers of (a)(ii) prior to step (b), or
  (2) the plurality of linear amplified nucleic acid fragments generated in step (b).

2. The method of claim 1, wherein said attachment feature is biotin.

3. The method of claim 1, wherein said solid substrate is selected from the group consisting of a bead, a microwell, and a surface.

4. The method of claim 1, wherein said plurality of random primers are hexamers, heptamers, octamers or nonamers.

5. The method of claim 1, wherein said plurality of nucleic acid fragments are derived from a biological sample selected from the group consisting of a single genome, a single nucleic acid library, and a single nucleic acid library insert sequence.

6. The method of claim 1, wherein each of said plurality of nucleic acid fragments is circularized.

7. A method, comprising:
 a) providing:
  i) a solid substrate that can be attached to at least one nucleic acid sequence bearing an attachment feature;
  ii) a plurality of random primers each bearing an attachment feature and lacking a universal sequence; and
  iii) a plurality of nucleic acid fragments, comprising a plurality of subsequences and lacking terminal universal sequences;
 b) annealing said plurality of nucleic acid fragments to said plurality of random primers under conditions that generate a plurality of linear amplified nucleic acid fragments incorporating said attachment feature; and
 c) combining the solid substrate under conditions that attach the solid substrate, through the attachment feature, with the plurality of random primers of (a)(ii) prior to step (b).

8. A method, comprising:
 a) providing:
  i) a solid substrate that can be attached to at least one nucleic acid sequence bearing an attachment feature;
  ii) a plurality of random primers each bearing an attachment feature and lacking a universal sequence; and
  iii) a plurality of nucleic acid fragments, comprising a plurality of subsequences and lacking terminal universal sequences, wherein each of said plurality of nucleic acid fragments is ligated to at least one barcode, thereby generating a barcoded nucleic acid fragment;
 b) annealing said plurality of nucleic acid fragments to said plurality of random primers under conditions that generate a plurality of linear amplified nucleic acid fragments incorporating said attachment feature; and
 c) combining the solid substrate under conditions that attach the solid substrate, through the attachment feature, with either
  (1) the plurality of random primers of (a)(ii) prior to step (b), or
  (2) the plurality of linear amplified nucleic acid fragments generated in step (b).

9. The method of claim 8, wherein said barcoded nucleic acid fragment is sequenced.

10. A method, comprising:
 a) providing:
  i) a solid substrate that can be attached to at least one nucleic acid sequence bearing an attachment feature;
  ii) a plurality of random primers each bearing an attachment feature and lacking a universal sequence; and
  iii) a plurality of nucleic acid fragments, comprising a plurality of subsequences and lacking terminal universal sequences, wherein said plurality of subsequences comprises a first subsequence having a first read pair sequence, and wherein said first read pair sequence comprises a first high throughput sequencing primer binding site;
 b) annealing said plurality of nucleic acid fragments to said plurality of random primers under conditions that generate a plurality of linear amplified nucleic acid fragments incorporating said attachment feature; and
 c) combining the solid substrate under conditions that attach the solid substrate, through the attachment feature, with either (1) the plurality of random primers of (a)(ii) prior to step (b), or (2) the plurality of linear amplified nucleic acid fragments generated in step (b).

11. The method of claim 10, wherein said method further provides a first high throughput sequencing primer.

12. The method of claim 11, wherein said method further comprises the step of annealing said first high throughput sequencing primer binding site to said first high throughput sequencing primer, under conditions such that said first read pair sequence is amplified.

13. The method of claim 10, wherein said plurality of subsequences comprises a second subsequence having a second read pair sequence, and wherein said second read pair sequence comprises a second high throughput sequencing primer binding site.

14. The method of claim 13, wherein said method further provides at least one primer selected from the group consisting of a first high throughput sequencing primer and a second high throughput sequencing primer.

15. The method of claim 14, wherein said method further comprises the step of annealing said second high throughput sequencing primer binding site to said second high throughput sequencing primer, under conditions such that said second read pair sequence is amplified.

16. The method of claim 14, wherein said first and second high throughput sequencing primers are compatible with ion semiconductor sequencing, pyrosequencing, polymerase-based sequence-by-synthesis, and ligation-based sequencing.

17. A method, comprising:

a) providing:

i) a solid substrate that can be attached to at least one nucleic acid sequence bearing an attachment feature;

ii) a plurality of random primers lacking a universal sequence, wherein the plurality of random primers comprises random primers bearing an attachment feature and random primers that do not bear an attachment feature, and wherein the ratio of random primers bearing the attachment feature to random primers not bearing the attachment feature is between 30:70 and 70:30; and iii) a plurality of nucleic acid fragments, each comprising a plurality of subsequences and lacking terminal universal sequences;

b) annealing said plurality of nucleic acid fragments to said plurality of random primers under conditions that generate a plurality of amplified nucleic acid fragments incorporating said attachment feature; and c) combining the solid substrate under conditions that attach the solid substrate, through the attachment feature, with either (1) the plurality of random primers of (a)(ii) prior to step (b), or (2) the plurality of amplified nucleic acid fragments after step (b).

* * * * *